(12) United States Patent
Chen et al.

(10) Patent No.: US 12,054,561 B2
(45) Date of Patent: Aug. 6, 2024

(54) ANTI-ANGIOGENESIS FUSION PROTEIN AND USES THEREOF

(71) Applicant: TRICAN BIOTECHNOLOGY CO., LTD, New Taipei (TW)

(72) Inventors: Huang-Tsu Chen, Cupertino, CA (US); Jiun-Shyang Leou, Hsinchu (TW); Chung-Yuan Hsu, Kaohsiung (TW); Cheng-Ke Li, Taoyuan (TW); Yun-Ting Wang, New Taipei (TW); Li-Tsen Lin, New Taipei (TW)

(73) Assignee: TRICAN BIOTECHNOLOGY CO., LTD, New Taipei (TW)

( * ) Notice: Subject to any disclaimer, the term of this patent is extended or adjusted under 35 U.S.C. 154(b) by 65 days.

(21) Appl. No.: 17/550,694

(22) Filed: Dec. 14, 2021

(65) Prior Publication Data

US 2022/0169750 A1 Jun. 2, 2022

Related U.S. Application Data

(62) Division of application No. 16/544,648, filed on Aug. 19, 2019, now Pat. No. 11,518,819.

(60) Provisional application No. 62/719,377, filed on Aug. 17, 2018.

(51) Int. Cl.
*C07K 16/46* (2006.01)
*C07K 14/71* (2006.01)
*C07K 16/22* (2006.01)

(52) U.S. Cl.
CPC ............ *C07K 16/468* (2013.01); *C07K 14/71* (2013.01); *C07K 16/22* (2013.01); *C07K 2317/21* (2013.01); *C07K 2317/31* (2013.01); *C07K 2317/34* (2013.01); *C07K 2317/52* (2013.01); *C07K 2317/55* (2013.01); *C07K 2317/622* (2013.01); *C07K 2317/76* (2013.01); *C07K 2317/94* (2013.01); *C07K 2319/30* (2013.01)

(58) Field of Classification Search
None
See application file for complete search history.

(56) References Cited

U.S. PATENT DOCUMENTS

| | | | | |
|---|---|---|---|---|
| 5,595,756 | A * | 1/1997 | Bally | A61K 9/1272 |
| | | | | 264/4.1 |
| 8,268,314 | B2 * | 9/2012 | Baehner | A61P 13/12 |
| | | | | 530/388.24 |
| 9,695,233 | B2 | 7/2017 | Duerr et al. | |
| 10,973,916 | B2 * | 4/2021 | Yang | C12N 15/79 |
| 2015/0023958 | A1 * | 1/2015 | Lee | A61P 9/00 |
| | | | | 435/254.2 |
| 2015/0023968 | A1 | 1/2015 | Lee et al. | |
| 2016/0289314 | A1 | 10/2016 | Shandilya et al. | |
| 2017/0275353 | A1 * | 9/2017 | Sheng | C07K 16/2818 |

FOREIGN PATENT DOCUMENTS

WO    WO 2017/001990 A1    1/2017

OTHER PUBLICATIONS

Sporn et al, "Chemoprevention of Cancer," Carcinogenesis, vol. 21 (2000), 525-530 (Year: 2000).*
Auerbach et al (Cancer and Metastasis Reviews, 2000, 19: 167-172) (Year: 2000).*
Gura T (Science, 1997, 278(5340): 1041-1042) (Year: 1997).*
Jain RK (Scientific American, Jul. 1994,58-65) (Year: 1994).*
Hogenesch et al (J Control Release. Dec. 10, 2012; 164(2): 183-186.) (Year: 2012).*
Koh et al (Cancer Cell: 18, 171-184, Aug. 17, 2010) (Year: 2010).*
Auerbach et al., "Angiogenesis assays: Problems and Pitfalls," Cancer and Metastasis Review, vol. 19, 2000, pp. 167-172.
Bork, "Powers and Pitfalls in Sequence Analysis: The 70% Hurdle," Genome Research, vol. 10, 2000, pp. 398-400.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, vol. 111. Nov. 1990, pp. 2129-2138.
Gura. "Systems for Identifying New Drugs Are Often Faulty," Science, vol. 278, No. 5340, Nov. 7, 1997, pp. 1041-1042.
Hogenesch et al., "Challenges in pre-clinical testing of anti-cancer drugs in cell culture and in animal models," J Control Release, vol. 164, No. 2, Dec. 10, 2012, pp. 183-186.
Jain, "Barriers to Drug Delivery in Solid Tumors," Scientific American, Jul. 1994, pp. 58-65.
Koh et al., "Double Antiangiogenic Protein, DAAP, Targeting VEGF-A and Angiopoietins in Tumor Angiogenesis, Metastasis, and Vascular Leakage," Cancer Cell, vol. 18, Aug. 17, 2010, pp. 171-184.
Lobner et al., "Engineered IgG1-Fc—One Fragment to Bind Them All," Immunological Reviews, vol. 270, No. 1. 2016 (Feb. 10, 2016), pp. 113-131.

(Continued)

*Primary Examiner* — Brian Gangle
*Assistant Examiner* — Andrea K McCollum
(74) *Attorney, Agent, or Firm* — Birch, Stewart, Kolasch & Birch, LLP

(57) ABSTRACT

The present invention provides a bi-functional fusion protein, (AT)a-Fc-(VT)b, simultaneously targeting vascular endothelial growth factor (VEGF) and angiopoietins (ANGs), wherein AT is an ANG binding motif; and VT is a VEGF binding motif, Fragment crystallizable region (Fc) is an N-terminal of Immunoglobulin G (IgG); each of a and b is an integer from 1 to 10. The bi-functional fusion proteins contain two or more domains of human proteins and are of all human sequences, and thus are expected to be non-immunogenic, and potentially can be used therapeutically in human targeting angiogenesis-associated diseases.

4 Claims, 14 Drawing Sheets
(10 of 14 Drawing Sheet(s) Filed in Color)
Specification includes a Sequence Listing.

(56) References Cited

OTHER PUBLICATIONS

Misoge et al., "Comparison of predicted and actual consequences of missence mutations," Proc Natl Acad Sci U S A, vol. 112, No. 37, Sep. 15, 2015, pp. E5189-E5198.
Skolnick et al., "From genes to protein structure and function; novel applications of Computation approaches in the genomic era," Trends Biotechnol., vol. 18, No. 1, Jan. 2000, pp. 34-39.
Sporn et al., "Chemoprevention of cancer," Carcinogenesis, vol. 21, No. 3, 2000, pp. 525-530.
Written Opinion of the International Searching Authority and International Search Report, dated Nov. 25, 2019, for International Application No. PCT/US2019/046996.

\* cited by examiner

ANTI-ANGIOGENESIS FUSION PROTEIN AND USES THEREOF

CROSS REFERENCE TO RELATED APPLICATIONS

This application is a Divisional of copending application Ser. No. 16/544,648, filed on Aug. 19, 2019, which claims priority under 35 U.S.C. § 119(e) to U.S. Provisional Application No. 62/719,377, filed on Aug. 17, 2018, all of which are hereby expressly incorporated by reference into the present application.

FIELD OF THE INVENTION

The present invention relates to an anti-angiogenesis fusion protein, which is a bi-functional fusion protein.

BACKGROUND OF THE INVENTION

Angiogenesis, the formation of blood vessels by sprouting from pre-existing ones, is essential for the growth of solid tumors and for tumor metastasis. The generation of new capillaries involves a multistep process, which includes the dissolution of the membrane of the originating vessel, the endothelial cell migration and proliferation, and formation of a new vascular tube. Suppression of any one of these steps would inhibit the formation of new vessels and therefore affect tumor growth and generation of metastases. Indeed, it has been estimated that the elimination of a single endothelial cell could inhibit the growth of tumor cells. It has been reported that anti-angiogenic therapies may provide a promising mechanism for cancer treatment.

Vascular endothelial growth factor (VEGF) plays an important role in the process of angiogenesis. New blood vessel formation in diseases such as age-related macular degeneration (AMD) or tumor growth is mainly caused by the overexpression of this key growth factor [Connolly et al. (1989) *J Clinic Invest* 84(5):1470-8; Ferrara et al. (1989) *Biochem Biophys Res Commun* 161(2):851-8; Ferrara et al. (1989) *Nat Med* 4(3):336-40]. The VEGF family comprises several members such as VEGF-A, VEGF-B, VEGF-C, VEGF-D, and placenta growth factor (PGF). VEGF-A is the prototypic member of the VEGF family and also the most studied member. VEGF-A has been shown to stimulate endothelial cell mitogenesis, promote cell survival and proliferation, induce cell migration, and increase microvascular permeability. Targeting angiogenesis process through blocking VEGF activities with antibodies, VEGF traps, or VEGF receptor (VEGFR) kinase inhibitor have been demonstrated to be effective preclinically and clinically to treat cancers, and AMD disease as well [Major et al. (1997) *J Pharmacol Exp. Ther* 283(1):402-10; Willett et al. (2004) *Nat Med* 10(2):145-7; Papadopoulos et al. (2012) *Angiogenesis* 15(2): 171-85; Aiello et al. (1995) *Proc. Natl. Acad. Sci. USA* 92(23):10457-61]. Among VEGF blockers, Eylea, for example, is an engineered chimeric Fc fusion protein containing the VEGFR1 extracellular Ig domain 2 (ECD, D2), VEGFR2 extracellular Ig domain 3 (ECD, D3) and IgG1 Fc fragment targeting VEGF-A, VEGF-B, and PGF, and currently approved by FDA to treat AMD and metastatic colorectal cancer [Holash et al. (2002) *Proc. Natl. Acad. Sci. USA* 99(17):11393-8].

Angiopoietins (ANGs) are a family of vascular growth factors also shown to play a critical role in angiogenesis [Alves et al. (2010) *BMC Infect Dis* 10:143-52]. Among which, ANG1 and ANG2 were demonstrated to be involved in balancing vessel stability and regression during both developmental and tumor-induced angiogenesis through the ANG-TIE signaling pathway [Augustin et al. (2009) *Nat Rev Mol Cell Biol* 10(3):165-77]. ANG1 and ANG2 bind to TIE2 with similar affinity [Suri et al. (1996) *Cell* 87(7): 1171-80; Maisonpierre et al. (1997) *Science* 277:55-60]. The TIE2 extracellular domain (ECD) contains three EGF-like modules that are flanked by two immunoglobulin (Ig)-like domains and a third Ig-like domain followed by three fibronectin type III (FNIII) repeats. Structure and function analysis revealed the ANG-binding site was located to the N-terminal pair of Ig-like subdomains, however, it was shown to have less binding activity as compared with that of entire TIE2 ECD [Lin et al. (1997) *J Clin Invest* 100:2072-2078]. Recent studies indicated ANG1 is an agonist promoting stabilization of vessels by maximizing interactions between endothelial cells and their surrounding support cells and the extracellular matrix. ANG2, on the other hand, was found to be a context-dependent antagonist that promotes angiogenic sprouting or vessel regression [Maisonpierre et al. (1997) *Science* 277:55-60]. Circulating ANG2 levels have been identified as factor predicting poor prognosis in many human cancers, including metastatic melanoma, colorectal cancer (CRC), and chronic lymphocytic leukemia [Eklund et al. (2013) *Exp Cell Res* 319(9):1271-80]. The elevated ANG2 was reported to cause endothelial destabilization, leading to vessel regression, hypoxia, and increased expression of both ANG2 and VEGF, which together induced robust angiogenesis in the tumor [Holash et al. (1999) *Science* 284(5422): 1994-8].

However, it is desirable to develop a new approach for inhibition of angiogenesis in treatment of angiogenesis-associated diseases.

BRIEF SUMMARY OF THE INVENTION

Accordingly, the present invention provides a fusion protein that inhibits an ANG-TIE signaling pathway and a VEGF-VEGFR signaling pathway, wherein the fusion protein contains an ANG inhibiting domain and a VEGF inhibiting domain thereby providing a significantly improved efficacy in inhibition of angiogenesis through blocking the interactions between ANG, VEGF, or both with their receptors.

In one aspect, the invention provides a bi-functional fusion protein comprising one or more ANG binding motif containing fragments and one or more VEGF binding motif containing fragments, which are fused with a linker, thereby providing a significantly improved efficacy in inhibition of angiogenesis through blocking the interactions between ANG, VEGF, or both with their receptors.

In one embodiment of the invention, the bi-functional fusion protein comprises (1) one or more ANG binding motif containing fragments and (2) one or more VEGF binding motif containing fragments, which are fused with a linker.

In one example of the invention, the ANG binding motif containing fragment is a fragment antigen-binding (Fab) fragment, and the VEGF binding motif containing fragment is a single chain antibody (ScFv)

In one embodiment of the invention, the bi-functional fusion protein is (AT)a-Fc-(VT)b, simultaneously targeting vascular endothelial growth factor (VEGF) and angiopoietins (ANGs), which provides a significantly improved anti-angiogenesis efficacy, wherein AT is an ANG binding motif, VT is a VEGF binding motif; Fc is a linker; each of a and b is an integer from 1 to 10.

In one embodiment of the invention, ANG binding motif is a fragment consisting of Tie2 extracellular domain (ECD) amino acid residues from 23-448.

In one embodiment of the invention, the VEGF binding motif is VEGFR1 ECD D2, VEGFR2 ECD D3, or a chimeric domain containing the both motifs. In one preferred embodiment, the VEGF binding motif is a chimeric domain containing VEGFR1 ECD D2 and VEGFR2 ECD D3.

In one embodiment of the invention, the linker is IgG1 Fc fragment, a short flexible GS linker or combination thereof.

In one embodiment of the invention, the bi-functional protein is a fusion protein, (AT)-Fc-(VT), wherein AT is an AT fragment containing a Tie2 ECD amino acid residues from 23-448, Fc is an IgG Fc fragment, and VT is a VT fragment containing a chimeric domain containing VEGFR1 D2 and VEGFR2 D3.

In one example of the invention, the AT fragment and IgG Fc fragment are fused, and then linked with the VT at the C-terminal of the AT-Fc fragment by a short flexible GS linker.

In one specific embodiment, the bi-functional fusion protein is constructed by a fragment antigen-binding (Fab) containing the ANG inhibiting domain and a single chain antibody (ScFv) having a VEGF inhibiting domain. Preferably, the Fab is an anti-Ang2 Fab, and the ScFv is a fusion fragment consisting of Lucentis Vh and Vk.

In one embodiment, the Fc fragment is a wild-type or a variant of any human immunoglobulin isotype, subclass, or allotype.

In a further aspect, the present invention provides a pharmaceutical composition comprising the fusion protein disclosed herein and a pharmaceutically acceptable carrier.

According to the invention, the pharmaceutical composition is used for preventing or treating an angiogenesis-associated disease, such as age-related macular degeneration (AMD) disease or a primary or metastatic cancer.

In a further yet aspect, the present invention provides a fusion protein capable of binding to angiopoietins, which contains Tie2 ECD amino acid residues from 23 to 448 fused with IgG1 Fc fragment.

In a further yet aspect, the present invention provides a fusion protein against VEGF, which contains a chimeric motif containing VEGFR1 D2 and VEGFR2 D3 fused with an IgG1 Fc fragment at the C-terminal thereof.

It is to be understood that both foregoing general description and the following detail description are exemplary and explanatory and are not restrictive of the invention.

BRIEF DESCRIPTION OF THE SEVERAL VIEWS OF THE DRAWINGS

The patent or application file contains at least one color drawing. Copies of this patent or patent application publication with color drawing will be provided by the USPTO upon request and payment of the necessary fee.

The foregoing summary, as well as the following detailed description of the invention, will be better understood when read in conjunction with the appended drawings. For the purpose of illustrating the invention, there are shown in the drawings embodiments which are presently preferred.

In the drawings:

Figure 1A:
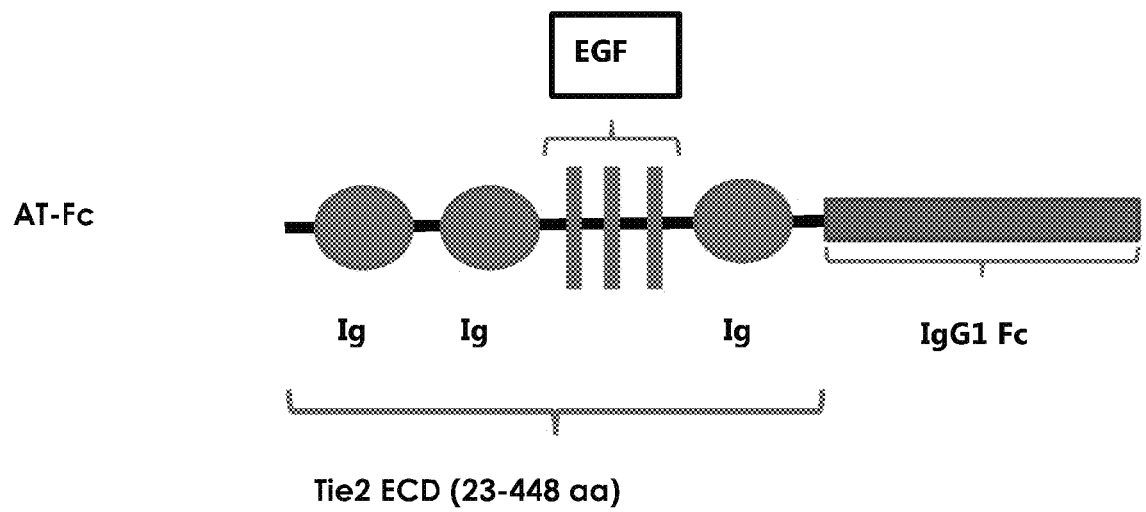
Figure 1B:
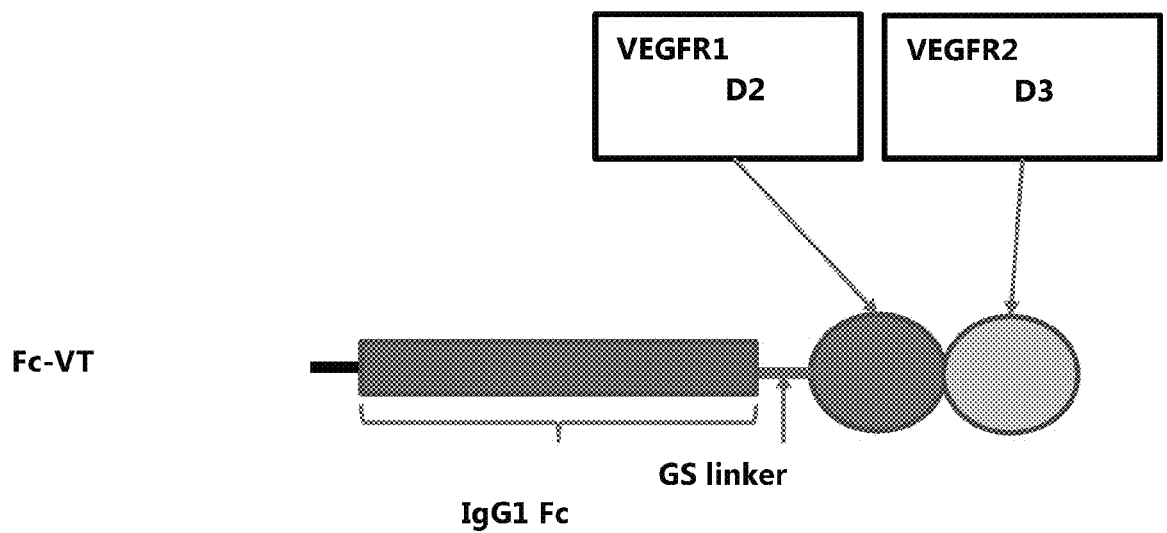

FIG. 1A and FIG. 1B show the structure diagrams of AT-Fc and Fc-VT proteins, respectively, in which the AT-Fc protein comprises a synthetic nucleotide sequence having the Tie2 ECD amino acid residues from 23 to 448 that contains the three Ig-like domains and three EGF-like repeats fused to the N-terminal of IgG Fc to construct the expression vector for AT-Fc protein; and the VT-Fc protein comprises the chimeric VEGF binding motifs consisting of VEGFR1 ECD D2 and VEGFR2 ECD D3, which was synthesized and fused to the C-terminal of the IgG Fc with a GS linker in between to create the expression vector for Fc-VT protein.

Figure 2A:
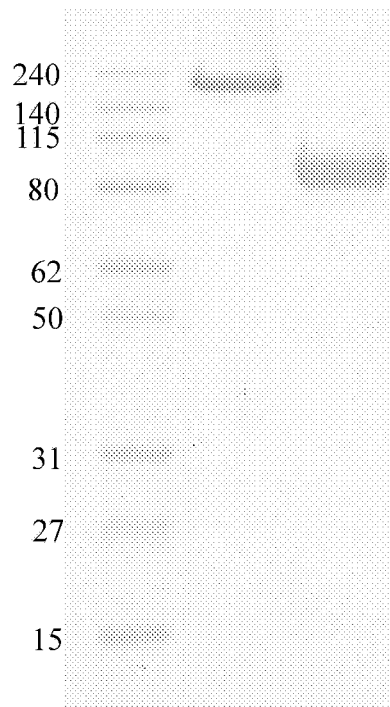
Figure 2B:
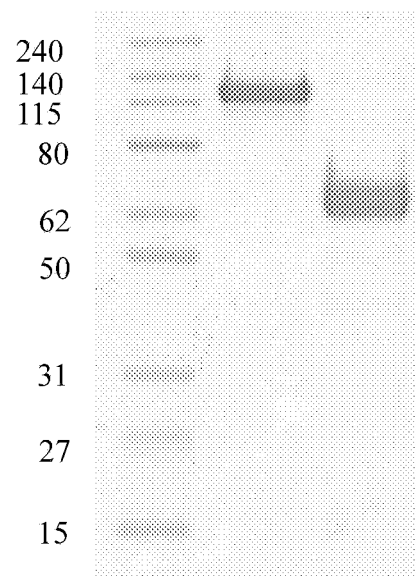

FIG. 2A and FIG. 2B show the PAGE analyses of the AT-Fc protein and the Fc-VT protein, respectively, wherein the AT-Fc and Fc-VT expression vectors were used to transfect HEK293 cells, separately, which were expressed and then purified from the cell culture supernatant using Protein G chromatography. The purified proteins (3 μg/lane) were gel-analyzed under reducing or non-reducing condition. FIGS. 2A and 2B show the results of the AT-Fc and Fc-VT proteins that were properly dimerized with a molecular weight about 160 kD and 130 kD, respectively, and greater than 90% purity were obtained by the single step Protein G chromatography to purify both fusion proteins. Lane 1, non-reduced; Lane 2, reduced.

Figure 3:
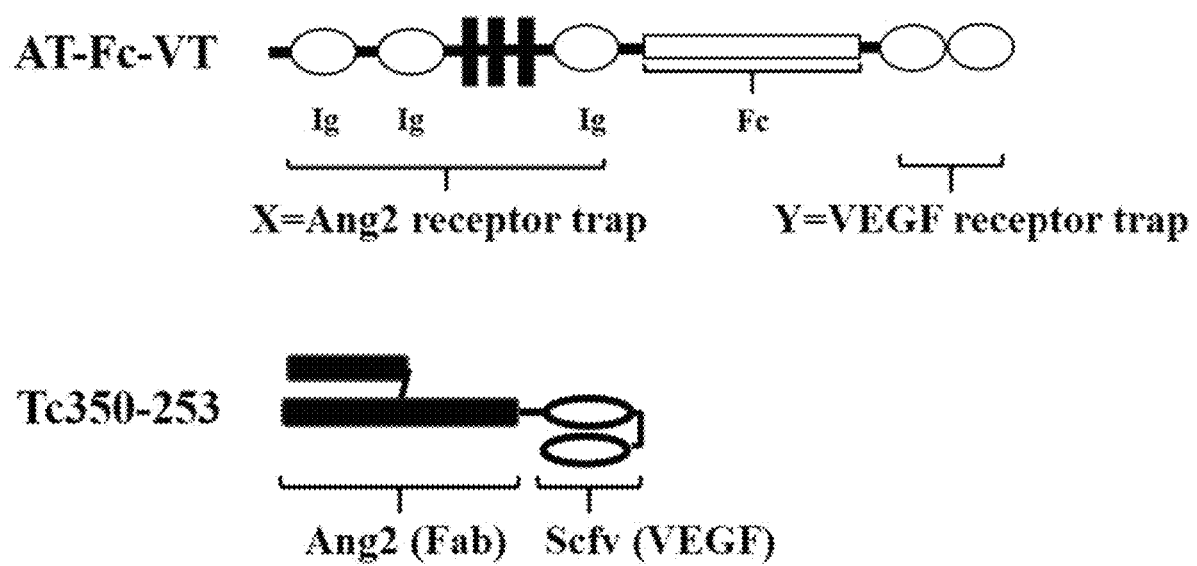

FIG. 3 shows the structure diagram of AT-Fc-VT and Tc350-253 bi-functional fusion proteins providing improved anti-angiogenesis activity.

Figure 4:
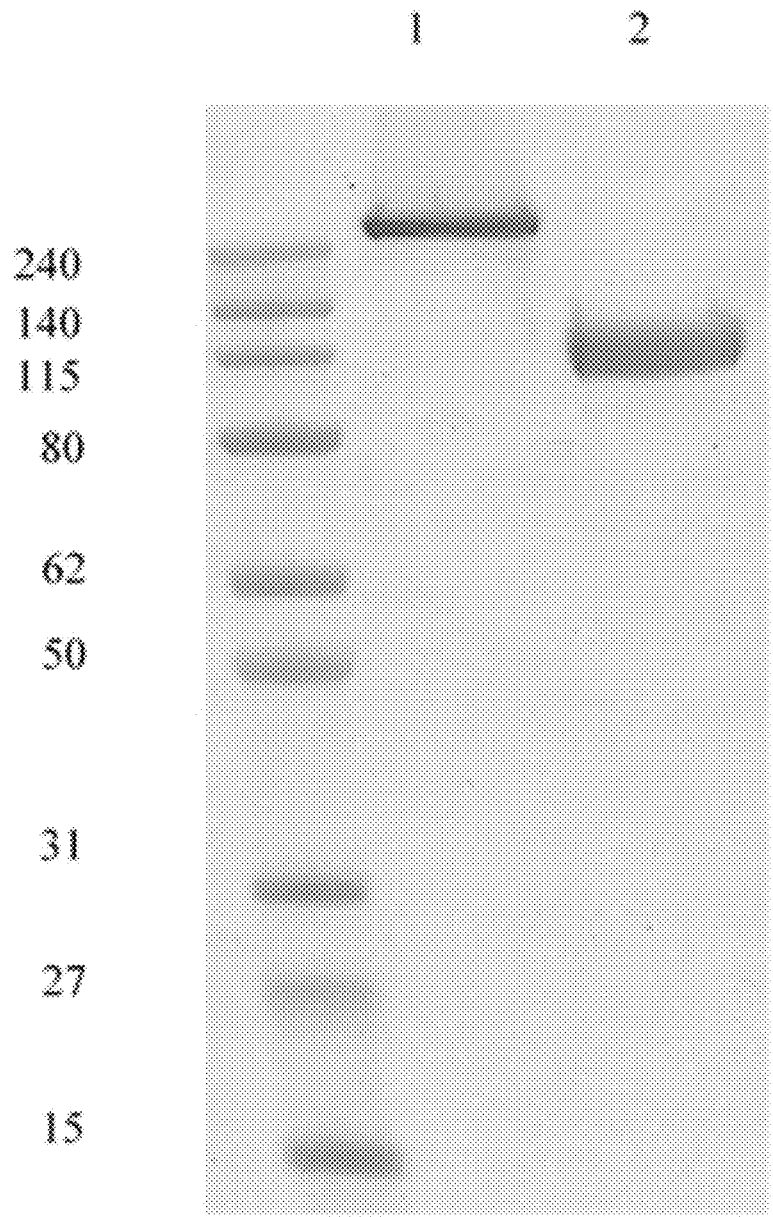

FIG. 4 shows the purified AT-Fc-VT bi-functional fusion protein, wherein the AT-Fc-VT expression vector was used to transfect HEK293 cells. Expressed soluble AT-Fc-VT fusion proteins were purified from cell culture supernatant using Protein G chromatography. The purified proteins (3 μg/lane) were then reduced or non-reduced before gel analysis. Results indicated fusion proteins were properly dimerized with molecular weight about 250 kD and >90% purity can be obtained by single step Protein G chromatography. Lane 1, non-reduced; Lane 2, reduced.

Figure 5:
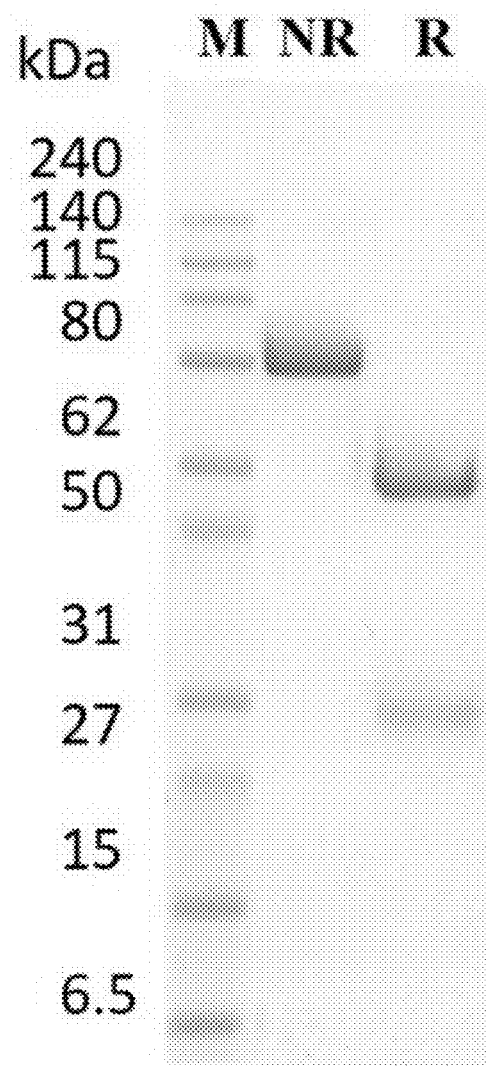

FIG. 5 shows the purified Tc350-253 bi-functional fusion protein. Tc350-253 protein was transiently expressed by HEK293 cells and purified from the transfected cell culture supernatant via nickel affinity chromatography. The purified protein (5 μg/lane) was gel-analyzed under reducing or non-reducing condition. The Tc350-253 bi-functional protein was properly expressed with a molecular weight about 75 kD, and greater than 90% purity was obtained. NR, non-reduced; R, reduced.

Figure 6:
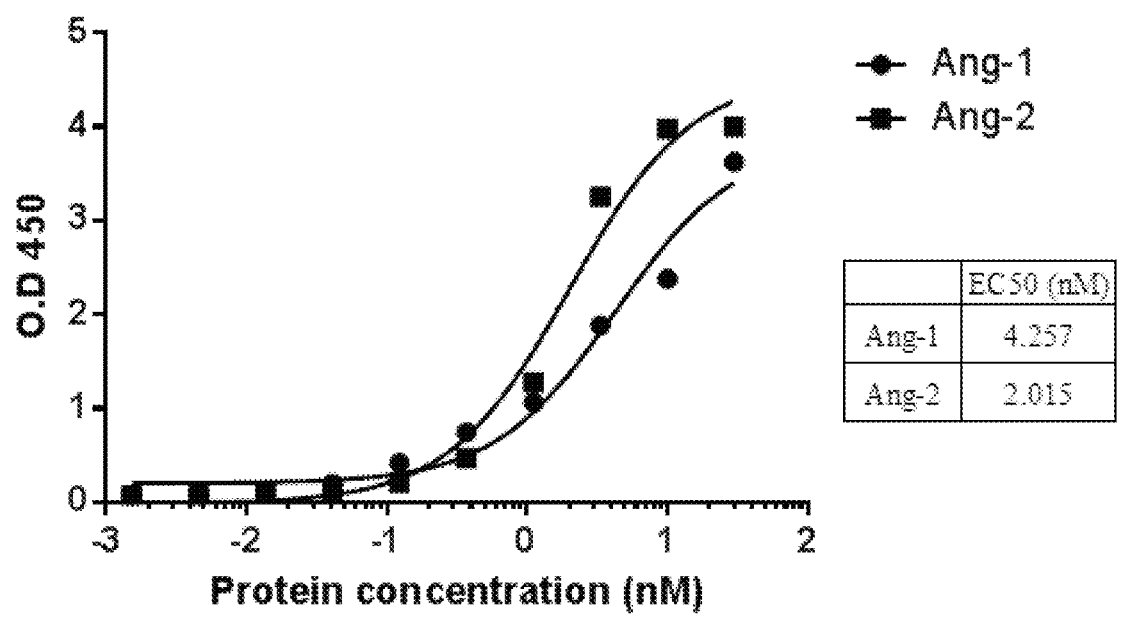

FIG. 6 shows the binding activity of the AT-Fc protein against ANG1 and ANG2 in direct ELISA assays. The ligand pre-coated wells were first incubated with various concentrations of purified AT-Fc protein. The bound proteins were then detected with HRP conjugated goat anti-human IgG Fc specific antibody and $OD_{450}$ readings were plotted; and the results indicated AT-Fc binds to ANG1 or ANG2 with $EC_{50}$ of 4.26 nM and 2.01 nM, respectively.

Figure 7:
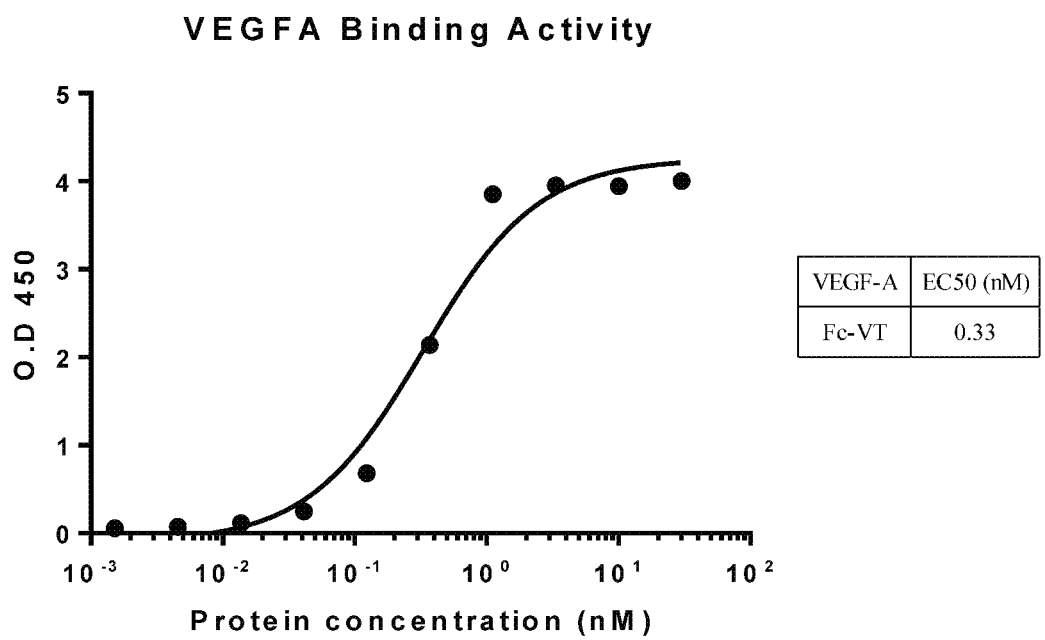

FIG. 7 shows the binding activity of the Fc-VT protein against VEGF-A. VEGF-A pre-coated wells were first incubated with various concentrations of purified Fc-VT proteins. The bound proteins after washing were detected with HRP conjugated goat anti-human IgG Fc specific antibody and $OD_{450}$ readings were plotted, and the results indicated Fc-VT binds to VEGF-A with $EC_{50}$ of 0.33 nM.

Figure 8:
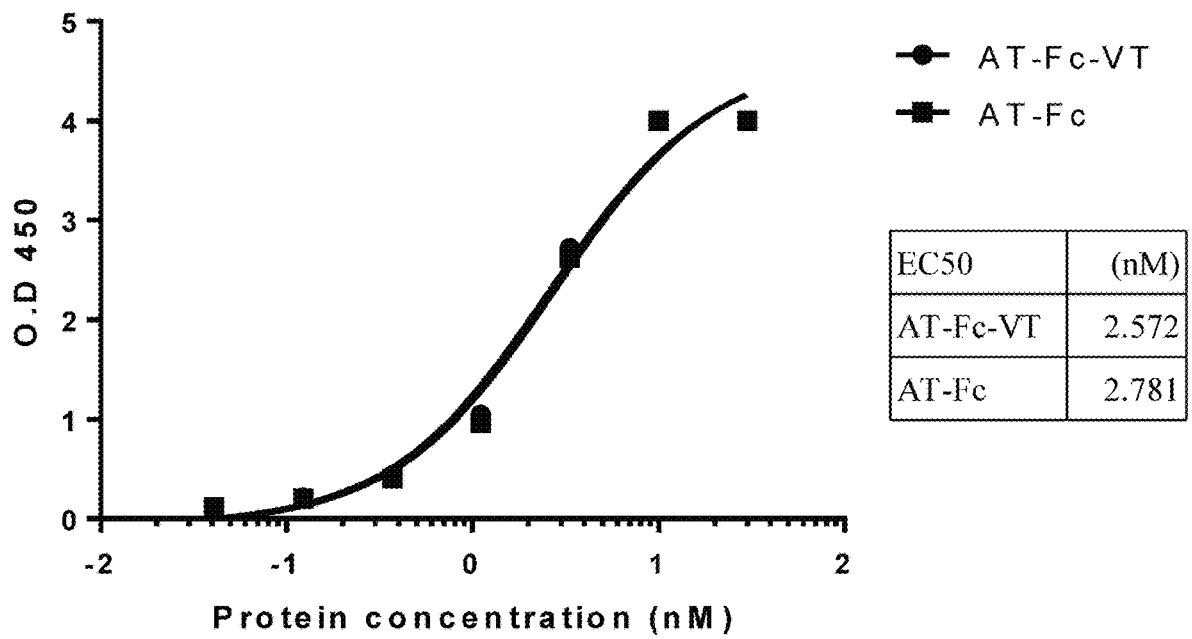
Figure 9:
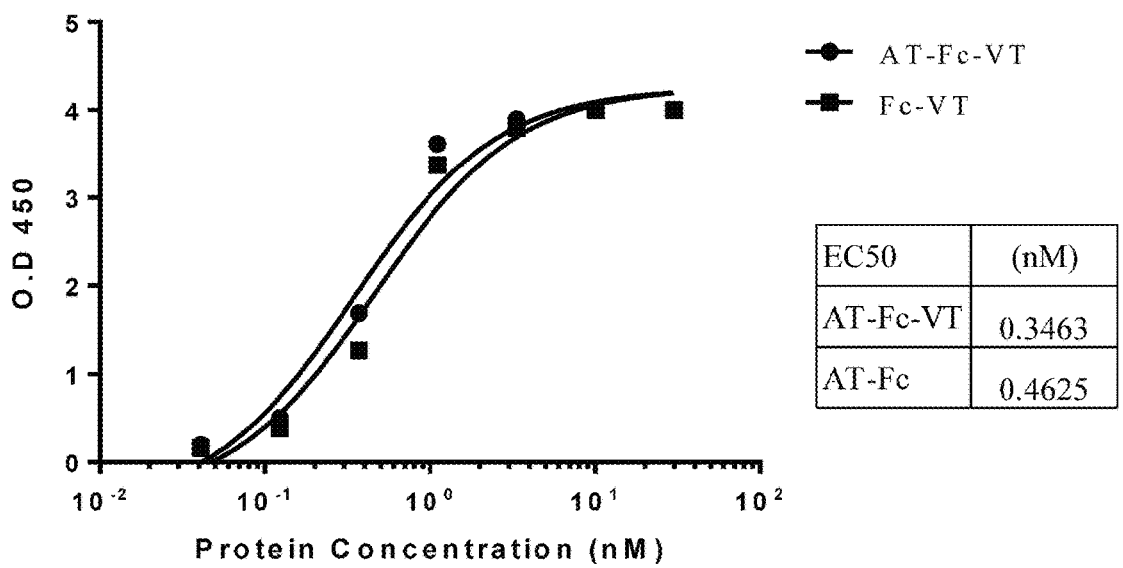

FIGS. 8 and 9 show the direct ligand binding activity of purified AT-Fc-VT fusion protein against ANG2 and VEGF-A, respectively. Ligand pre-coated wells were first incubated with various concentrations of purified AT-Fc-VT protein. The bound proteins were then detected with HRP conjugated goat anti-human IgG Fc specific antibody and $OD_{450}$ readings were plotted. The results indicated AT-Fc-VT is able to bind ANG2 and VEGF-A with $EC_{50}$ of 2.57 nM and 0.35 nM, respectively, which was comparable to the binding activity of AT-Fc (0.28 nM) or Fc-VT (0.46 nM).

Figure 10:
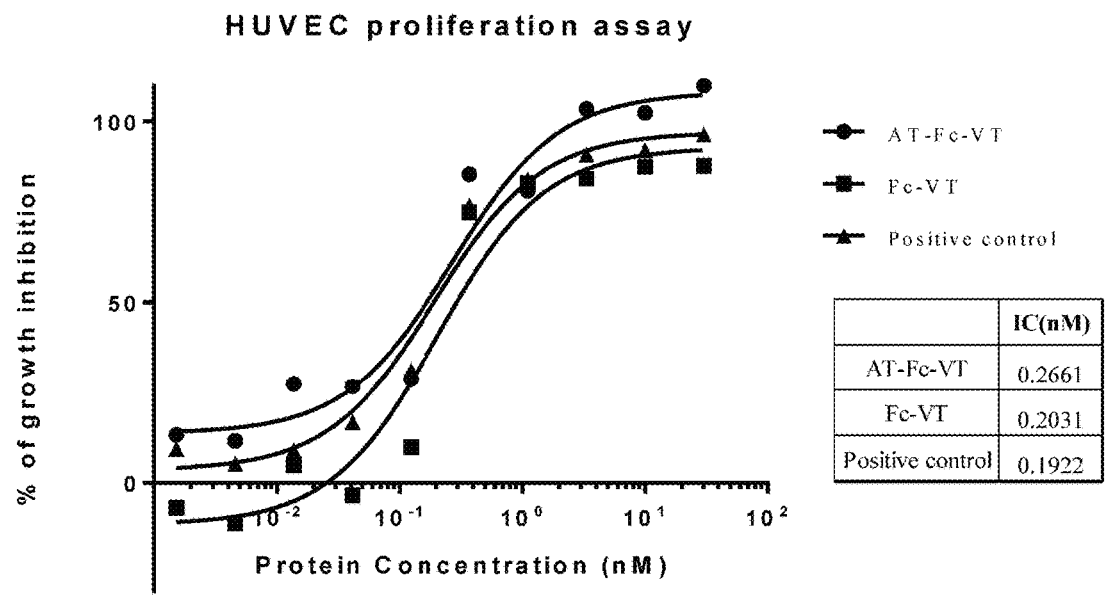

FIG. 10 shows the inhibitory effect of fusion proteins on VEGF-dependent HUVEC cell growth assay. Human umbilical vein endothelial cells are used to demonstrate VEGF-dependent cell growth inhibition by binding of fusion proteins, Fc-VT and AT-Fc-VT, to VEGF. In the experiment, HUVECs are maintained in the Endothelial Cell Growth Medium (Lonza, Inc.) with 2% FBS. A 96-well flat bottom microtiter plate is coated with collagen, and then incubated with 50 µl of 1 nM of VEGF-A (R&D systems, Inc.) and various concentrations of fusion proteins, Fc-VT or AT-Fc-VT, in each well for 1 hour at 37° C. before adding 50 µl of HUVECs at $1\times10^5$ cells/ml in Medium-199 (10% FBS, Hyclone, Inc.). After incubate for 72 hours at 37 C with 5% CO2, cell proliferation was assayed by adding 10 µl of MTS detection reagent (Promega Inc.) to each well and then measuring OD absorption at 450/650 nm. In this experiment. Results indicated both Fc-VT and AT-Fc-VT have similar inhibitory activities against VEGF as comparable with Fc-VT (0.27 nM vs. 0.20 nM). In this study, a positive control, VEGFR1 ECD D2 and VEGFR2 ECD D3 fused C-terminally with IgG1 Fc fragment, was also included and shown to have $IC_{50}$ of 0.19 nM.

Figure 11:
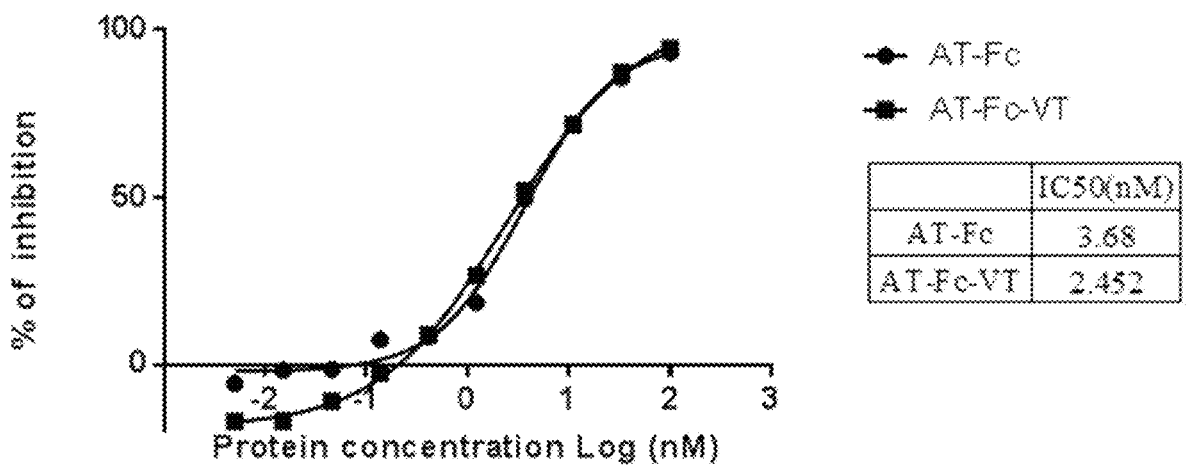

FIG. 11 shows the soluble ANG2 binding analysis. The purified fusion proteins, AT-Fc and AT-Fc-VT, were used to examine the ANG2 binding activity in this assay. The 100 µl of AT-Fc or AT-Fc-VT (1 µg/ml) fusion proteins was coated onto 96-well ELISA plates (NUNC®) for overnight at 4° C. The coated wells were blocked with 1% BSA in PBS for 1 hour at room temperature (RT). Three-fold serial diluted AT-Fc or AT-Fc-VT starting from 100 nM were incubated with equal volume of 500 pM recombinant ANG2 (PEPROTECH®) for 2 hr at RT before transferred to 96-well with coated protein. After incubation, transferred sample to each respective well and incubated for 1 hr at RT. The plate was washed three times with washing buffer (ABCAM®) and incubated with Biotinylated anti-ANG2 antibody (ABCAM®) for 1 hr at RT. After washing, the plate was incubated with streptavidin-HRP (ABCAM®) for 45 min at RT. After final washing, tetramethylbenzidine (TMB) was added and absorbance was measured at 450 nm using a plate reader. Data were analyzed using Prism (GRAPHPAD®) to calculate percentage of inhibition.

Figure 12:
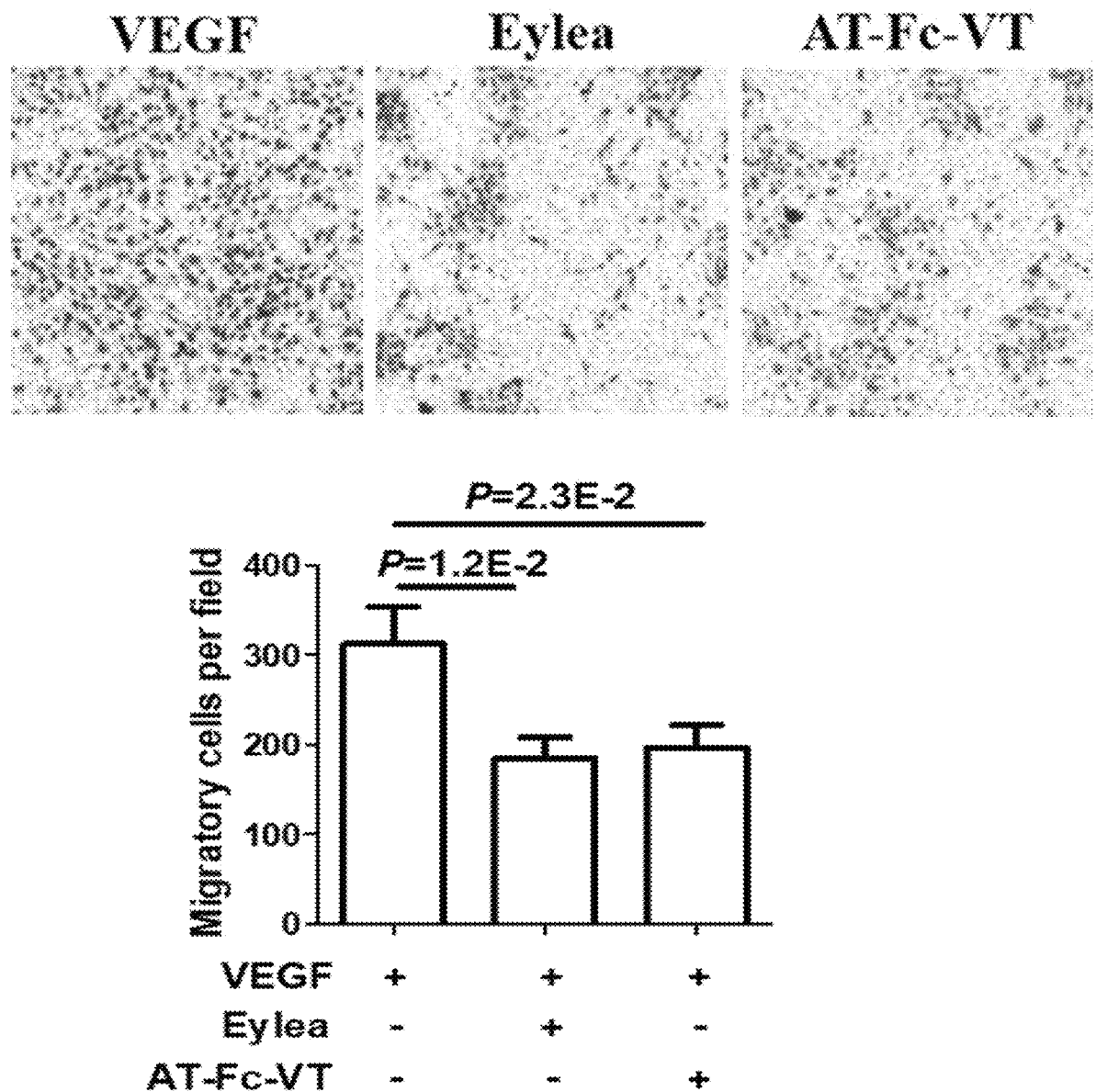

FIG. 12 shows the inhibition of VEGF-induced endothelial cell migration by bi-functional fusion protein.

Figure 13:
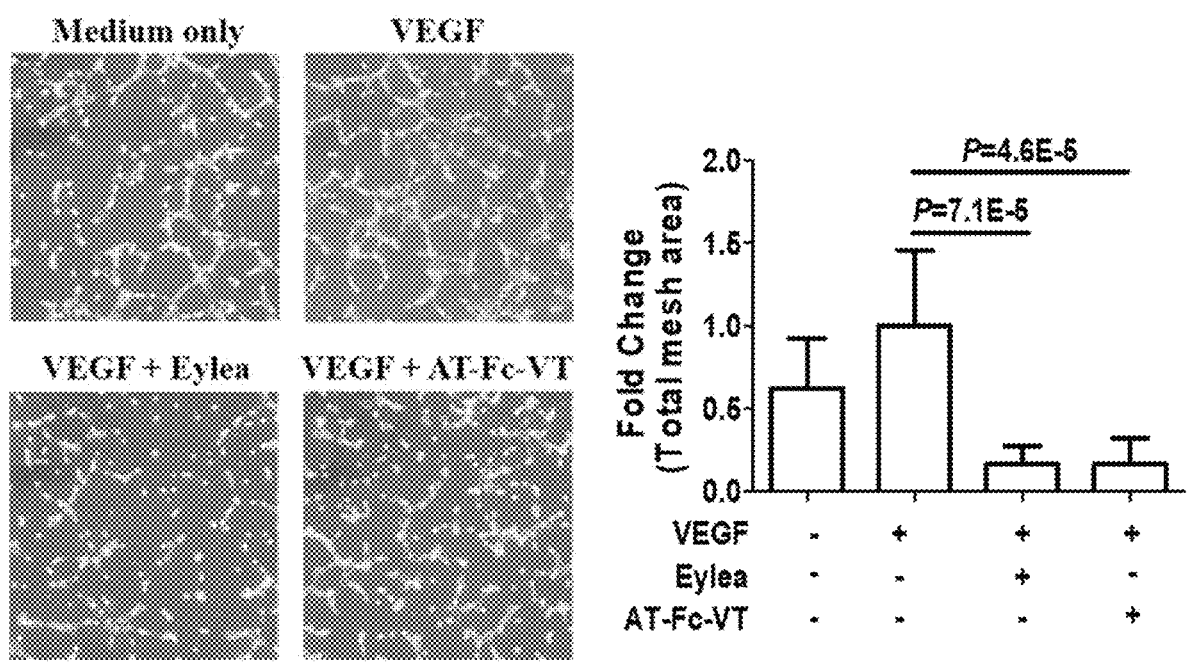

FIG. 13 shows the inhibition of VEGF-induced endothelial cell tube formation by bi-functional fusion protein.

Figure 14:
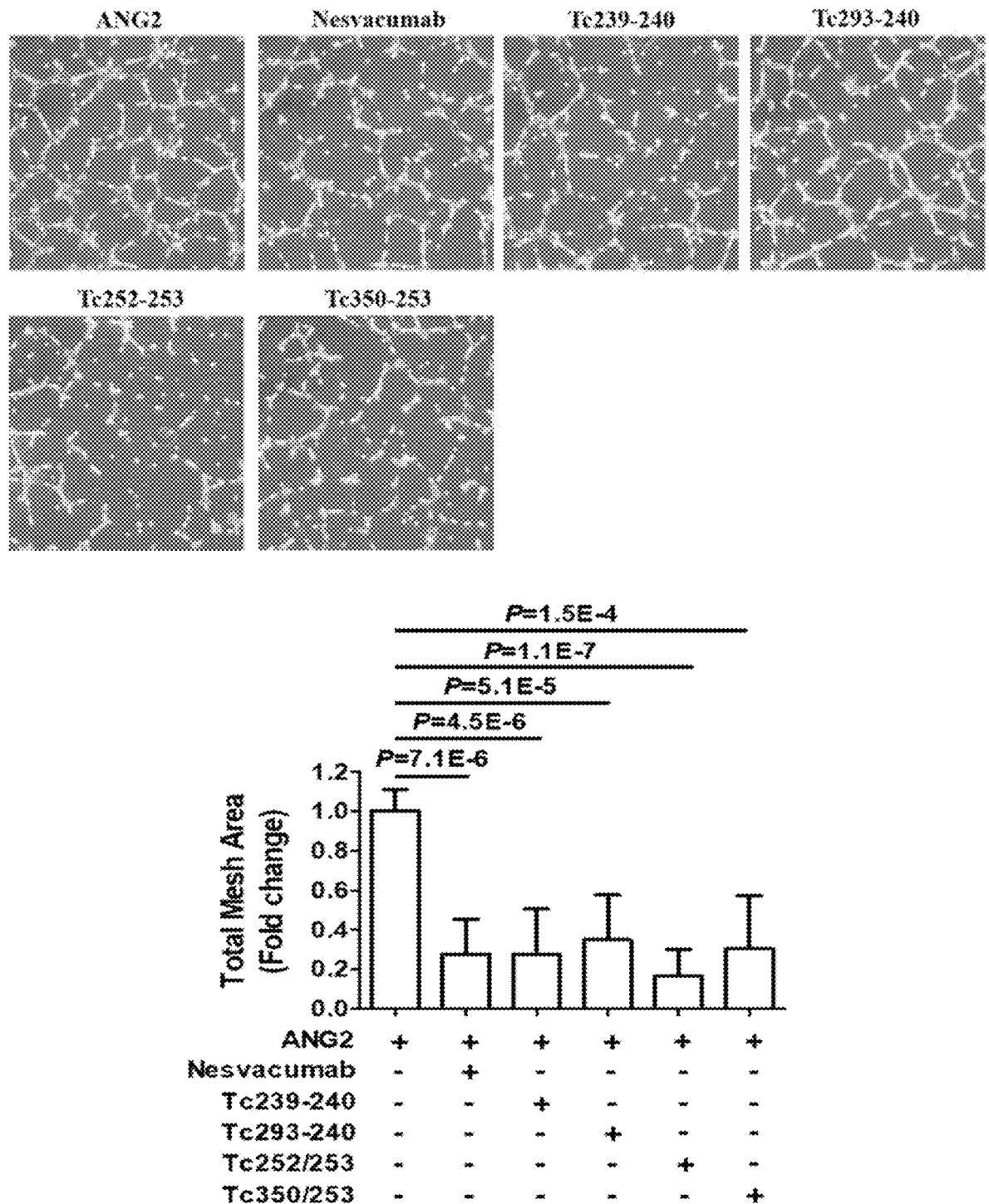

FIG. 14 shows the inhibition of ANG2-induced endothelial tube formation by bi-functional protein Tc350-253.

Figure 15:
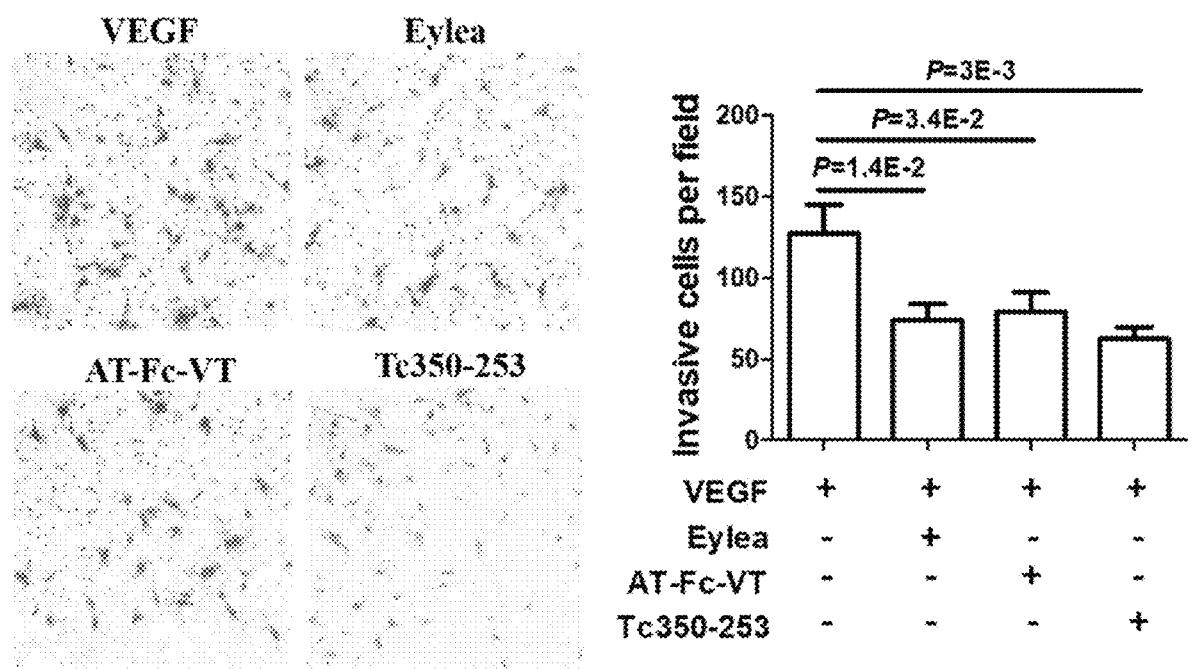

FIG. 15 shows the inhibition of VEGF-induced endothelial cell invasion by bi-functional angiogenesis blockers.

Figure 16:
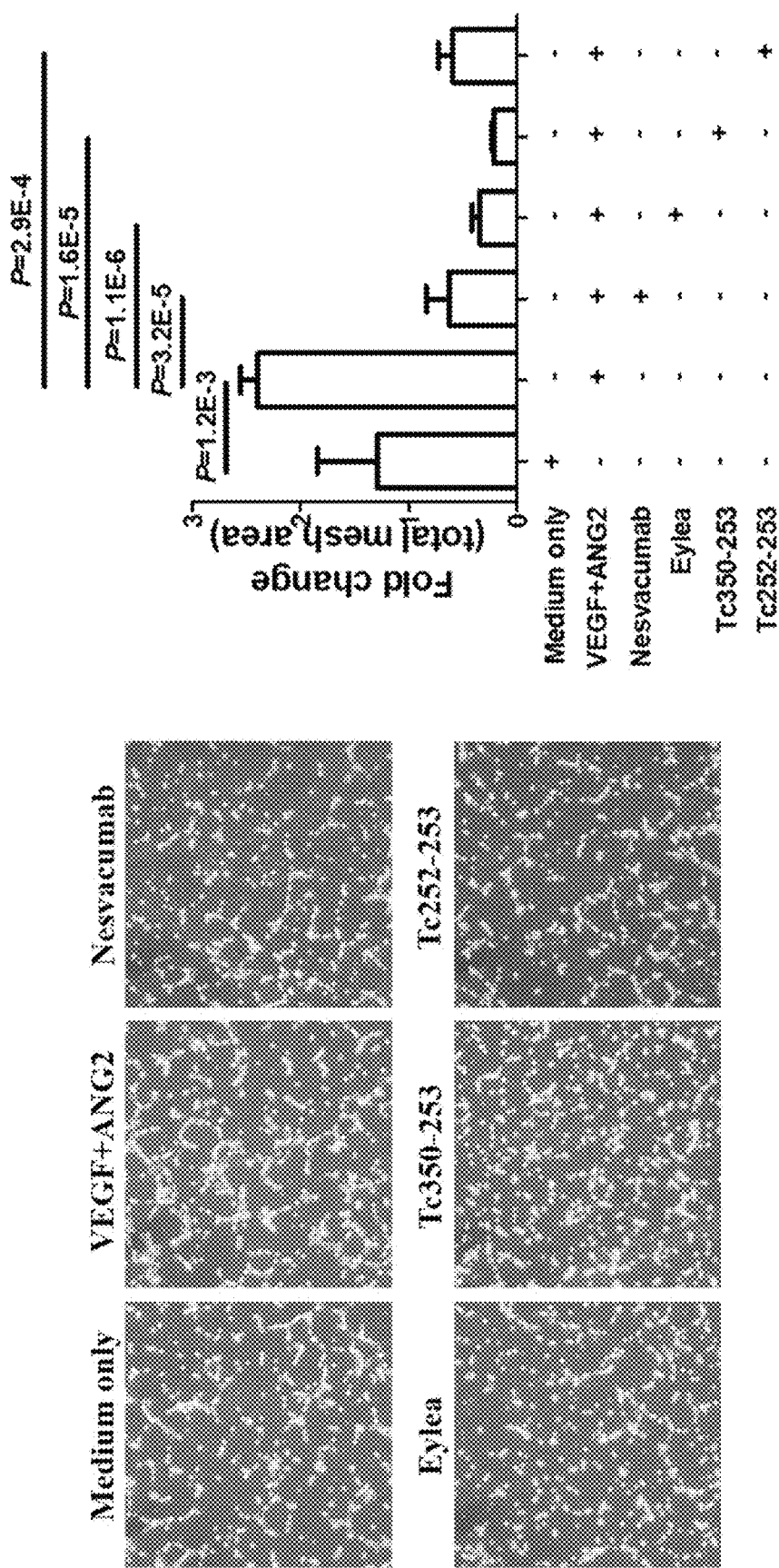

FIG. 16 shows the inhibition of VEGF/ANG2-induced endothelial cell tube formation by bi-functional protein T350-253.

Figure 17:
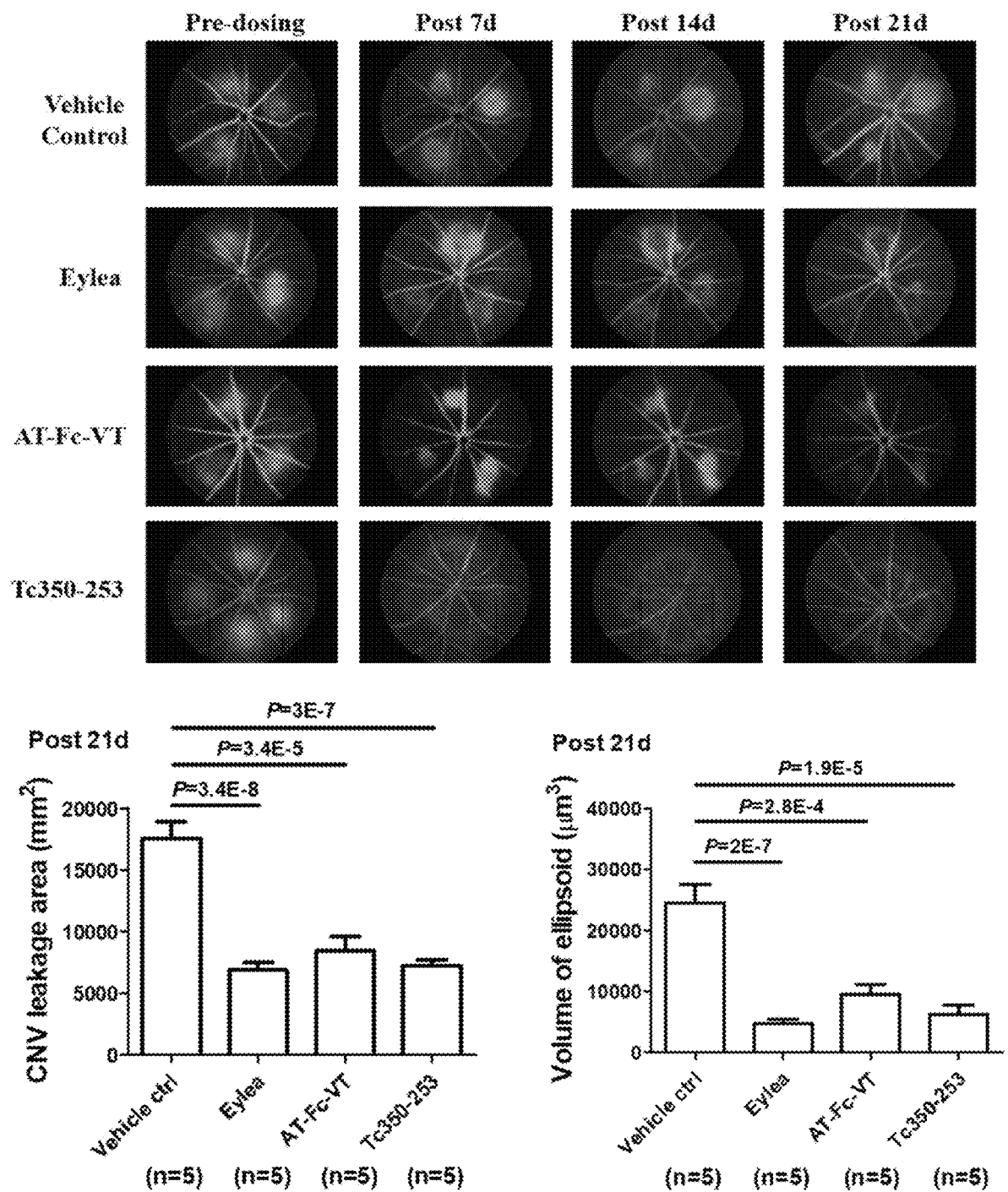

FIG. 17 shows the inhibition of laser-induced choroidal neovascularization (CNV) in mice by bi-functional proteins.

DETAILED DESCRIPTION OF THE INVENTION

Unless otherwise defined herein, scientific and technical terms used herein have the meanings that are commonly understood by those of ordinary skill in the art.

As used herein, the term "antibody" is a protein consisting of one or more polypeptides substantially encoded by immunoglobulin genes. A typical antibody is a tetramer that is composed of two identical pairs of polypeptide chains, each pair having one "light" and one "heavy" chain.

The term "antibody variable region" as used herein refers to an N-terminal region of an antibody variable chain comprising amino acid residues that are primarily responsible for antigen recognition. Those of ordinary skill in the art are readily able to identify an antibody variable region and to determine the minimum size needed to confer antigen recognition. The antibody variable region may be a single chain antibody, for example a single chain Fv antibody (scFv) in which a variable heavy chain region and a variable light chain region are joined together (directly or through a peptide linker) to form a continuous polypeptide. The scFv antibody may be chemically synthesized or may be expressed from a nucleic acid including $V_H$- and $V_L$-encoding sequences either joined directly or joined by a peptide-encoding linker.

The invention provides a bi-functional fusion protein that inhibits an angiopoietin (ANG)-TIE signaling pathway and a vascular endothelial growth factor (VEGF)-vascular endothelial growth factor receptor (VEGFR) signaling pathway. In the invention, the fusion protein contains an ANG inhibiting domain and a VEGF inhibiting domain thereby providing a significantly improved efficacy in inhibition of angiogenesis through blocking the interactions between ANG, VEGF, or both with their receptors.

In the invention, the both VEGF and ANG playing a crucial role in the process of angiogenesis, were used for construction of IgG Fc fusion blockers. The AT-Fc and Fc-VT proteins having ANG and VEGF binding activity, respectively, were first generated, and AT-Fc-VT bi-functional protein was created to provide a bi-functional fusion protein (with ANG and VEGF binding activities) accordingly. These AT-Fc and Fc-VT proteins were shown to be able to bind its respective ligands with high affinity, and also to provide anti-ANG and anti-VEGF functions in cell-based assays, respectively. In the invention, the Fc fusion protein contains the domains of human proteins and are of all human origins, and are expected to be non-immunogenic, and thus, potentially can be further developed as therapeutics for treating angiogenesis-associated diseases.

In the invention, any motif, peptide, protein, or fragment having blocking VEGF activity may be used, for example anti-VEGF antibodies, VEGF traps, or VEGF receptor (VEGFR) extracellular Ig domains such as D1-D7, in particular, VEGFR1 extracellular Ig domain 2 (ECD, D2), VEGFR2 extracellular Ig domain 3 (ECD, D3).

In the invention, any motif, peptide, protein, or fragment binding to angiopoietin (ANG) may be used, for example, ANG1 and ANG2 binding to TIE2. The TIE2 ECD contains three EGF-like modules that are flanked by two immunoglobulin (Ig)-like domains and a third Ig-like domain followed by three fibronectin type III (FNIII) repeats. The ANG-binding site was located to the N-terminal pair of Ig-like subdomains.

Since VEGF and ANG2 were upregulated in a variety of cancer cell types, blocking the ANG-TIE interaction together with/without VEGF blocker, a bi-functional fusion against ANG2 and VEGF is created in this invention for treatment of cancers and age-related macular degeneration (AMD) disease.

In various embodiments, angiogenesis-associated diseases may be age-related macular degeneration (AMD) disease, or a primary and metastatic cancer.

The age-related macular degeneration (AMD) disease is a disease that blurs the sharp, central vision as needed for "straight-ahead" activities such as reading, sewing and driving. Normally, AMD affects the macula, the part of an eye.

The primary and metastatic cancers may be carcinomas of breast, colon, rectum, lung, oropharynx, hypopharynx, esophagus, stomach, pancreas, liver, gallbladder and bile ducts, small intestine, urinary tract (including kidney, bladder and urothelium), female genital tract (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma), tumors of the brain, nerves, eyes, and meninges (including astrocytomas, gliomas, glioblastomas, retinoblastomas, neuromas, neuroblastomas, Schwannomas, and meningiomas), tumors arising from hematopoietic malignancies, acute leukemia, acute lymphoblastic leukemia (ALL), acute myeloid leukemia (AML), B cell lymphoma, Burkitt's lymphoma, chronic myelocytic leukemia (CML), chronic lymphocytic leukemia (CLL), hairy cell leukemia, Hodgkin's and non-Hodgkin's lymphomas, hematopoietic malignancies, Kaposi's sarcoma, malignant lymphoma, malignant histiocytosis, malignant melanoma, multiple myeloma, paraneoplastic syndrome/hypercalcemia of malignancy, or solid tumors.

In one embodiment of the invention, a fragment having Tie2 ECD amino acid residues from 23 to 448 (SEQ ID NO: 1) was used to generate an AT-Fc protein with IgG1 Fc fragment (SEQ ID NO: 2) at C-terminal to engineer an AT-Fc protein.

In another embodiment of the invention, a fragment containing the VEGFR1 D2 and VEGFR2 D3 chimeric motifs (SEQ ID NO: 3) was fused at the C-terminal of the IgG1 Fc fragment (SEQ ID NO: 2) to construct an Fc-VT protein with a short flexible GS linker (SEQ ID NO: 4) between them to ensure that the folding is correct and steric hindrance is minimized.

In one yet embodiment, the AT-Fc-VT fusion protein was engineered through fusion to obtain a domain containing VEGFR1 ECD D2 and VEGFR2 ECD D3 (SEQ ID NO: 3) at C-terminal of AT-Fc also included with a GS linker (SEQ ID NO: 4) between the AT-FC and VT proteins.

In a specific embodiment, the bi-functional protein Tc350-253 was engineered and expressed as a disulfide-linked Tc350-Tc253 protein, wherein Tc350 was constructed by fusing Lucentis variable heavy chain domain (Vh) (SEQ ID NO: 5) and variable kappa domain (Vk) (SEQ ID NO: 6) at the C-terminal of Anti-Ang2-Fragment antigen-binding (Fab) heavy chain (HC) (SEQ ID NO: 7) with the short flexible GS linker (SEQ ID NO: 4) in between, and Tc253 was constructed to have Anti-Ang2-Fab light chain (LC) fragment (SEQ ID NO: 8).

In further embodiment, all fusion proteins described in this invention were leaded by a signal peptide (SEQ ID NO: 9) for the secretion of expressed proteins.

The amino acid sequences of the AT-Fc, Fc-VT, AT-Fc-VT, and Tc350 were those set forth in SEQ ID NO: 10, SEQ ID NO: 11, SEQ ID NO: 12, and SEQ ID NO: 13, respectively.

In the present invention, the above-mentioned AT-Fc and/or Fc-VT proteins were transiently expressed by HEK293 cells and purified from the transfected cell culture supernatant via Protein G chromatography. It was found that the products having a purity greater than 90% were obtained in a single step purification process and all fusion proteins were properly formed and expressed.

According to the present invention, the bi-functional fusion protein, AT-Fc-VT, simultaneously targeting VEGF and ANGs was created through fusing the VEGF binding motif at the C-terminal of the ANG protein. As shown in the results, the AT-Fc-VT fusion protein according to the invention provided a bi-functional efficacy in inhibiting VEGF-dependent HUVEC cell proliferation, cell migration, tube formation as well as to bind ANG2 protein, as comparable with Fc-VT or AT-Fc protein respectively.

According to the present invention, the bi-functional protein Tc350-253 provides a beneficial effect on VEGF and/or ANG2-induced angiogenesis-associated phenotypes. Particularly, the bi-functional protein Tc350-253 unexpectedly improves laser-induced choroidal neovascularization, which has been used extensively in studies of the exudative form of age-related macular degeneration (AMD).

So that the disclosure may be more readily understood, select terms are defined below.

As used herein, the term "fusion protein" refers to a protein created through the connection of two or more binding proteins, or motifs, or peptides/amino acid fragments coding for different genes, the translation of which genes results in a single or multiple polypeptides with multi-functional properties derived from each of the original proteins. A fusion protein can include a protein conjugated to an antibody, an antibody conjugated to a different antibody, or an antibody conjugated to a Fab fragment.

Each of the AT or VT fragment is an antibody, or a fragment of antibody with long half-life in vivo.

As used herein, the term "linker" refers to an amino acid residue or fragment, or a polypeptide comprising two or more amino acid residues joined by peptide bonds that are used to link two peptides, polypeptides or proteins. The linker may be a Fc fragment, which is an immunoglobulin Fc region of a wild-type or a variant of a human immunoglobulin isotype, subclass, or allotype thereof.

The term "Fc region" defines the C-terminal region of an immunoglobulin heavy chain of an antibody. The Fc region may be a native sequence Fc region or a variant Fc region.

As used herein, the term "pharmaceutical composition" refers to a composition or a formulation comprising the fusion protein according to the invention, which can be prepared by mixing the fusion protein according to the invention with optional pharmaceutically acceptable carriers, including solvents, dispersion media, isotonic agents and the like. The carrier can be liquid, semi-solid or solid carriers. In some embodiments, carriers may be water, saline solutions or other buffers (such as serum albumin and gelatin), carbohydrates (such as monosaccharides, disaccharides, and other carbohydrates including glucose, sucrose, trehalose, mannose, mannitol, sorbitol, or dextrins), gel, lipids, liposomes, resins, porous matrices, binders, fillers, coatings, stabilizers, preservatives, antioxidants (including ascorbic acid and methionine), chelating agents (such as EDTA), salt forming counter-ions (such as sodium), non-ionic surfactants [such as TWEEN®, PLURONICS® or polyethylene glycol (PEG)], or combinations thereof.

In some embodiments, the pharmaceutical composition further comprises one additional therapeutic agent for preventing or treating said disease or disorder to be treated. For example, the additional agent may be a therapeutic agent, a chemotherapeutic agent; an imaging agent, a cytotoxic agent, an angiogenesis inhibitor, a kinase inhibitor, a co-stimulation molecule blocker (including but not limited to anti-B7.1, anti-B7.2, CTLA4-Ig, anti-CD20), an adhesion molecule blocker (including but not limited to an anti-LFA-1 antibody, an anti-E/L selectin antibody, a small molecule inhibitor), and an anti-cytokine antibody or functional fragment thereof (including but not limited to an anti-IL-18, an anti-TNF, and an anti-IL-6/cytokine receptor antibody).

The invention is further illustrated by the following examples, which should not be construed as further limiting.

EXAMPLES

Example 1 Expression and Purification of Angiogenesis Blockers

The TIE2 ECD amino acid residues from 23-448 was used as ANG binding motif, and the chimeric domains with VEGFR1 D2 and VEGFR2 D3 were used as VEGF binding trap. The corresponding DNAs were synthesized and fused with IgG1 Fc fragment gene at C-terminal for ANG blocker (AT-Fc) (FIG. 1A) or at N-terminal for VEGF blocker (Fc-VT) (FIG. 1B) with a short flexible GS linker was placed in between. To construct bi-functional AT-Fc-VT expression vector, AT-Fc was fused with GS linker and the VEGF motif, sequentially, at C-terminal (FIG. 3). These fusion constructs were cloned to pCI-neo (Promega, Inc.) expression vector between the EcoR I and Not I restriction sites under the control of a CMV promoter. The vector contains a Neomycin resistant gene and an Ampicillin resistant gene for mammalian cell selection and $E.$ $coli$ propagation. All fusion constructs contained a signal peptide at the N-terminal for the secretion of soluble fusion proteins. These expression constructs were used to transfect 50 ml of HEK293 cells at density of $1 \times 10^6$ cells per ml transiently. The culture media was harvested after 96 hours of transfection and fusion proteins were purified via Protein G chromatography.

As shown in FIGS. 2 and 4, about 3 mg fusion proteins (per transfection) having a purity greater than 90% was obtained.

To construct bi-functional protein Tc350-253 expression vector (FIG. 3), Anti-Ang2 Fab HC was sequentially fused with Lucentis Vh and Lucentis Vk separated by GS linker. Tc350-253 protein was transiently expressed by HEK293 cells and purified from the transfected cell culture supernatant via nickel affinity chromatography. The purified protein (5 μg/lane) was gel-analyzed under reducing or non-reducing condition. The Tc350-253 bi-functional protein was properly expressed with a molecular weight about 75 kD, and greater than 90% purity was obtained (FIG. 5).

Example 2 In Vitro Binding of Angiogenesis Blockers

Overnight ligand pre-coated (100 ng/well) wells were washed 3 times with 1×PBS and blocked with 400 ul 5% non-fat skin milk in PBS for 2 hr. After blocking, 100 ul of 3-fold serially diluted purified protein started from 30 nM were added to each corresponding well in duplicate and incubated for 1 hr at room temperature on shaker. After binding, wells were washed 3 times with PBST (1×PBS with 0.1% TWEEN-20®) before adding 100 ul of 1:2500 diluted goat anti-human IgG Fc HRP conjugates (Jackson ImmunoResearch Inc.) to each well and incubated on shaker for another hour. After final washing, TMB reagent (Invitrogen, Inc.) was added and OD absorption at 450 nm was measured. The data analyzed by sigmoidal curve fitting using Prism 4. Binding of AT-Fc, Fc-VT, and AT-Fc-VT to ANG or VEGF were assessed by similar assays.

As shown in FIG. 6, the calculated $EC_{50}$ for AT-Fc against ANG1 and ANG2 are 4.26 nM and 2.01 nM, respectively. The results collected herein indicated the soluble extracellular domain (amino acid residues 23-448) is functionally active in angiopoietin binding and could modulate the activity of the membrane-bound form by competing for angiopoietins.

As shown in FIG. 7, the Fc-VT had the anti-VEGF efficacy in the VEGF-A binding assessment. The calculated $EC_{50}$ against VEGF-A was 0.33 nM. As shown in the results as collected, the C-terminally localized VEGFR1 D2 and VEGFR2 D3 chimeric VEGF trap was functional with high affinity and could neutralize VEGF's biological activities.

As shown ion FIGS. 8 and 9, the binding activities to ANG2 and VEGF of the purified AT-Fc-VT bi-functional fusion protein were assessed and the results indicated that the AT-Fc-VT fusion protein was able to bind ANG2 and VEGF-A with $EC_{50}$ of 2.57 nM and 0.35 nM, respectively, and provided significantly improved binding activities as compared with the AT-Fc against ANG2, and the Fc-VT against VEGF.

In conclusion, the AT-Fc-VT fusion protein were confirmed to have bi-functions to modulate the ANG-TIE and VEGF-VEGFR pathways through the inhibition of ligand binding and receptor activation.

Example 3 Inhibition of VEGF-Dependent HUVEC Proliferation Assay by Angiogenesis Blockers The Fc-VT and AT-Fc-VT were used to inhibit VEGF activities in a cell base assay. Human Umbilical Vein Endothelial Cells (HUVEC cells, Lonza, Inc.) were used to demonstrate VEGF-dependent cell proliferation which can be inhibited by VEGF blocker. In the experiment, HUVECs were maintained in the Endothelial Cell Growth Medium (Lonza, Inc.) with 2% FBS. Collagen pre-coated wells were loaded with 50 ml of 1 nM of VEGF-A (R&D systems, Inc.) and various concentrations of Fc-VT or AT-Fc-VT per well for 1 hour at 37° C. before adding 50 ml of HUVECs at $1 \times 10^5$ cells/ml in Medium-199 (10% FBS, Hyclone, Inc.) to each well. After 72 hours incubation at 37 C with 5% CO2, the cell growth was assayed by adding 10 ml MTS detection reagent (Promega Inc.) to each well and then measuring OD absorption at 450/650 nm.

As shown in FIG. 10, the 50 percent inhibitory activity ($IC_{50}$) of AT-Fc-VT on VEGF-dependent HUVEC cell proliferation assay was 0.26 nM, similar to that of Fc-VT (0.20 nM) in this example.

Example 4 Inhibition of Endothelial Cell Tube Formation by Angiogenesis Blockers The AT-Fc and AT-Fc-VT were used to determine the anti-ANG2 activities in the tube formation assay. Human umbilical vein endothelial cells were used to demonstrate Ang2-dependent cell tube formation which can be inhibited by binding of AT-Fc or AT-Fc-VT to Ang2. HUVECs are maintained in the Endothelial Cell Growth Medium (Lonza, Inc.) with 2% FBS. Prior to assay, HUVEC cells were cultivated in basal media without serum for 2 hr, and then trypsinized and re-suspended in 1% serum at $10^5$ cells/ml. $1.5 \times 10^4$ cells were seeded per Matrigel pre-coated well, and 200 ng/ml Ang2 with/without AT-Fc or AT-Fc-VT at various concentrations. After incubation at 37° C. for 18 hr, document tube formation with 3 non-overlapping images taken from each well repeated in triplicates (9 images/sample). The tube length was calculated using the ImagePro software (Media Cybernetics Inc.).

As shown in FIG. 11, the 50 percent inhibitory activity (IC$_{50}$) of AT-Fc-VT on tube formation was 2.45 nM, less than that of AT-Fc (3.68 nM) in this example.

Example 5 Bi-Functional Fusion Protein AT-Fc-VT Significantly Inhibits VEGF-Induced Endothelial Cell Migration The inhibitory effect of the bi-functional protein AT-Fc-VT on VEGF-induced chemotaxis was assessed using HUVECs on transwell plates (8-μm pore size, Costar). HUVEC cells (1×10$^5$) with M199 serum-free medium were placed in the upper well. The ligand human VEGF (0.2 μg/ml) were mixed with Eylea (2 μg/ml) or AT-Fc-VT (2 μg/ml) in 10% FBS M199 medium and placed in the lower well. The transwell plate were incubated for 24 h in a 5% incubator to allow cells from the upper well to transmigrade towards the bottom chamber. The membrane inserts were then fixed and stained with 1% crystal violet. Cells adhered to the lower surface of membrane inserts were visualized via microscopy and the average number of migrated cells was calculated from five representative fields on triplicate inserts using ImageJ software.

We examined the effect of AT-Fc-VT protein on the physiological responses of endothelial cells to VEGF stimulation. HUVEC cells were added to the upper chambers and were exposed to VEGF with vehicle, VEGF with Eylea, VEGF with AT-Fc-VT, individually. After 24 h, cells that migrated to the lower chamber of the membrane were counted. VEGF significantly increased the migration of HUVEC cells. However, the angiogenesis blocker AT-Fc-VT significantly inhibited the migration induced by VEGF (FIG. 12).

Example 6 Bi-Functional Fusion Protein AT-Fc-VT Inhibits VEGF-Induced HUVEC Cells Tube Formation To study the function of bi-functional angiogenesis blocker AT-Fc-VT in angiogenesis, an in vitro Matrigel tube formation assay was performed in human umbilical vein endothelial cells. HUVEC cells were incubated in basal media without serum for 2 hr, and then trypsinized by accutase. 4×10$^3$ HUVEC cells were seeded onto Matrigel pre-coated wells containing VEGF (1 μg/ml) with AT-Fc-VT (100 μg/ml) or Eylea (100 μg/ml) at 37° C. for 4.5 hr. Quantification of endothelial network formation was performed by Image J angiogenesis system (5 images/sample).

Under VEGF treatment, when cultured on Matrigel for 4.5 hr, HUVEC cells displayed a primary a vascular tubular network. However, bi-functional protein AT-Fc-VT significantly disrupted the formation of tubular structures (FIG. 13).

Example 7 Bi-Functional Protein Tc350-253 Inhibits ANG2-Induced Tube Formation of HUVEC Cells HUVEC cells were incubated in basal media without serum for 2 hr. 4×10$^3$ HUVEC cells were seeded onto Matrigel pre-coated wells containing ANG2 (0.5 μg/ml) with Tc350-253 (50 ROM) or Tc293-240 (50 μg/ml) at 37° C. for 4.5 hr. Quantification of endothelial network formation was performed by Image J angiogenesis system (5 images/sample).

Higher levels of ANG2 correlate with disease severity in human wet Age-related Macular Degeneration (AMD) and cancer progression including angiogenesis, metastasis and inflammation. We generated an innovative design to co-targeting VEGF and Ang2. To address the function of bi-functional protein in angiogenesis, an in vitro Matrigel tube formation assay was performed. The result indicated that bi-functional proteins Tc350-253 or Tc293-240 suppress ANG2-induced HUVEC cells tube formation in vitro (FIG. 14).

Example 8 Bi-Functional Proteins AT-Fc-VT and Tc350-253 Inhibit VEGF-Induced HUVEC Cell Invasion The invasion assay was performed by precoating the transwell inserts with Matrigel Basement Membrane Matrix (BD Biosciences, San Diego, CA, USA), according to the manufacturer's instructions. HUVEC cells (2×10$^5$) with Medium-199 were placed in the upper well. The ligand human VEGF (0.2 μg/ml) were mixed with Eylea (2 μg/ml), AT-Fc-VT (2 μg/ml) or Tc350-253 (2 μg/ml) in the lower chamber, individually. The transwell plate were incubated for 24 h in a 5% incubator to allow cells from the upper well to transmigrate towards the bottom chamber. The membrane inserts were then fixed and stained with 1% crystal violet. Cells adhered to the lower surface of membrane inserts were visualized via microscopy and the average number of migrated cells was calculated using ImageJ software.

The bi-functional proteins of AT-Fc-VT and Tc350-253 were used to determine the anti-VEGF activities using boyden chamber invasion assay. Similar to the results of the migration study, the angiogenesis blockers AT-Fc-VT and Tc350-253 inhibited the invasive ability induced by VEGF (FIG. 15).

Example 9 Bi-Functional Protein Tc350-253 Inhibits VEGF/ANG2-Induced HUVEC Cells Tube Formation HUVEC cells were incubated in basal media without serum for 2 hr, and then trypsinized by accutase. 4×10$^3$ HUVEC cells were seeded onto Matrigel pre-coated wells containing VEGF (0.5 μg/ml)/ANG2 (0.5 μg/ml) with Eylea (50 μg/ml), Tc350-253 (50 μg/ml) or other anti-Ang2 antibodies (50 μg/ml) individually at 37° C. for 4.5 hr. Quantification of endothelial network formation was performed by Image J angiogenesis system (5 images/sample).

To study the function of dual-targeting protein Tc350-253 in angiogenesis, an in vitro Matrigel tube formation assay was performed in human umbilical vein endothelial cells. Bi-functional angiogenesis blocker Tc350-253 significantly disrupted the formation of tubular structures (FIG. 16). The bioactivity of bi-functional protein Tc350-253 was better than Eylea or anti-Ang2 antibodies (Nesvacumab and Tc252-253) in this assay.

Example 10 Bi-Functional Proteins AT-Fc-VT and Tc350-253 Inhibit Neovascularization in Laser-Induced Choroidal Neovascularization (CNV) Mouse Model Laser-induced CNV was used animal model for wet AMD to assess the activities of angiogenesis blockers. After mice were anesthetized with ketamine hydrochloride (100 mg/kg body weight) and the pupils were dilated with 1% tropicamide, three burns of 532 nm diode laser photocoagulation were delivered to each retina. Burns were performed in the 9, 12, and 3 o'clock positions of the posterior pole of the retina. Production of a bubble at the time of laser, indicating rupture of Bruch's membrane, was an important factor in obtaining CNV.

In the laser-induced CNV model, male C57BL/6 mice were intravitreally injected with vehicle control, EYLEA® (40 μg), AT-Fc-VT (40 μg) or Tc350-253 (40 μg) in the right eye on day 1 (n=5/group). The retinal angiogenesis was examined by fluorescein angiography and optical coherence tomography on day 0, 7, 14 and 21. For fluorescein angiography, 10% sodium fluorescein was injected intravenously and serial images were captured immediately (every 10 s for 10 min). The injected sodium fluorescein is completely excreted after 24 h. Images were captured using the Micron III retinal imaging microscope (Phoenix Research Laboratories, San Ramon, CA, USA) to determine the extent of CNV formation. For OCT analysis, ellipsoid volume was calculated by the formula V=4/3 πabc where a (width), b (depth) and c (length) are the radii of the horizontal plane or vertical plane of the ellipsoid.

VEGF and ANG-2 appear strongly linked to pathological neovascularization and vascular permeability, which are the hallmarks of ocular neovascular disease. We tested the effect of bi-functional proteins AT-Fc-VT or Tc350-253 on angiogenesis by laser-induced choroidal neovascularization mouse model. It showed the bi-functional proteins AT-Fc-VT and Tc350-253 significantly inhibit neovascularization in this model using fundus fluorescein angiography (FFA) analysis (FIG. 17). Quantification of laser-CNV lesions as ellipsoids by optical coherence tomography (OCT) also showed a significant reduction in lesion volume after bi-functional proteins AT-Fc-VT or Tc350-253 treatment (FIG. 17).

While the present invention has been disclosed by way preferred embodiments, it is not intended to limit the present invention. Any person of ordinary skill in the art may, without departing from the spirit and scope of the present invention, shall be allowed to perform modification and embellishment. Therefore, the scope of protection of the present invention shall be governed by which defined by the claims attached subsequently.

---

The invention claimed is:

1. A bi-functional fusion protein that inhibits an angiopoietin (ANG)-TIE signaling pathway and a vascular endothelial growth factor (VEGF)-vascular endothelial growth factor receptor (VEGFR) signaling pathway having the amino acid sequence set forth in SEQ ID NO: 13.

2. A pharmaceutical composition comprising the bi-functional fusion protein of claim 1 and a pharmaceutically acceptable carrier.

3. The pharmaceutical composition of claim 2, which is for preventing or treating age-related macular degeneration (AMD) disease.

4. The pharmaceutical composition of claim 2, which is for inhibiting cancer angiogenesis.

* * * * *

SEQUENCE LISTING

```
<160> NUMBER OF SEQ ID NOS: 13

<210> SEQ ID NO 1
<211> LENGTH: 426
<212> TYPE: PRT
<213> ORGANISM: Homo sapiens

<400> SEQUENCE: 1

Ala Met Asp Leu Ile Leu Ile Asn Ser Leu Pro Leu Val Ser Asp Ala
1               5                   10                  15

Glu Thr Ser Leu Thr Cys Ile Ala Ser Gly Trp Arg Pro His Glu Pro
            20                  25                  30

Ile Thr Ile Gly Arg Asp Phe Glu Ala Leu Met Asn Gln His Gln Asp
        35                  40                  45

Pro Leu Glu Val Thr Gln Asp Val Thr Arg Glu Trp Ala Lys Lys Val
    50                  55                  60

Val Trp Lys Arg Glu Lys Ala Ser Lys Ile Asn Gly Ala Tyr Phe Cys
65                  70                  75                  80

Glu Gly Arg Val Arg Gly Glu Ala Ile Arg Ile Arg Thr Met Lys Met
                85                  90                  95

Arg Gln Gln Ala Ser Phe Leu Pro Ala Thr Leu Thr Met Thr Val Asp
            100                 105                 110

Lys Gly Asp Asn Val Asn Ile Ser Phe Lys Lys Val Leu Ile Lys Glu
        115                 120                 125

Glu Asp Ala Val Ile Tyr Lys Asn Gly Ser Phe Ile His Ser Val Pro
    130                 135                 140

Arg His Glu Val Pro Asp Ile Leu Glu Val His Leu Pro His Ala Gln
145                 150                 155                 160

Pro Gln Asp Ala Gly Val Tyr Ser Ala Arg Tyr Ile Gly Gly Asn Leu
                165                 170                 175

Phe Thr Ser Ala Phe Thr Arg Leu Ile Val Arg Arg Cys Glu Ala Gln
            180                 185                 190

Lys Trp Gly Pro Glu Cys Asn His Leu Cys Thr Ala Cys Met Asn Asn
        195                 200                 205

Gly Val Cys His Glu Asp Thr Gly Glu Cys Ile Cys Pro Pro Gly Phe
    210                 215                 220

Met Gly Arg Thr Cys Glu Lys Ala Cys Glu Leu His Thr Phe Gly Arg
```

```
                225                 230                 235                 240
Thr Cys Lys Glu Arg Cys Ser Gly Gln Glu Gly Cys Lys Ser Tyr Val
                245                 250                 255

Phe Cys Leu Pro Asp Pro Tyr Gly Cys Ser Cys Ala Thr Gly Trp Lys
                260                 265                 270

Gly Leu Gln Cys Asn Glu Ala Cys His Pro Gly Phe Tyr Gly Pro Asp
                275                 280                 285

Cys Lys Leu Arg Cys Ser Cys Asn Asn Gly Glu Met Cys Asp Arg Phe
                290                 295                 300

Gln Gly Cys Leu Cys Ser Pro Gly Trp Gln Gly Leu Gln Cys Glu Arg
305                 310                 315                 320

Glu Gly Ile Gln Arg Met Thr Pro Lys Ile Val Asp Leu Pro Asp His
                    325                 330                 335

Ile Glu Val Asn Ser Gly Lys Phe Asn Pro Ile Cys Lys Ala Ser Gly
                340                 345                 350

Trp Pro Leu Pro Thr Asn Glu Glu Met Thr Leu Val Lys Pro Asp Gly
                355                 360                 365

Thr Val Leu His Pro Lys Asp Phe Asn His Thr Asp His Phe Ser Val
                370                 375                 380

Ala Ile Phe Thr Ile His Arg Ile Leu Pro Pro Asp Ser Gly Val Trp
385                 390                 395                 400

Val Cys Ser Val Asn Thr Val Ala Gly Met Val Glu Lys Pro Phe Asn
                405                 410                 415

Ile Ser Val Lys Val Leu Pro Lys Pro Leu
                420                 425

<210> SEQ ID NO 2
<211> LENGTH: 228
<212> TYPE: PRT
<213> ORGANISM: Homo sapiens

<400> SEQUENCE: 2

Ala Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
                35                  40                  45

Ser His Glu Asp Pro Glu Val Lys Phe Asn Trp Tyr Val Asp Gly Val
                50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
                100                 105                 110

Pro Ile Glu Lys Thr Ile Ser Lys Ala Lys Gly Gln Pro Arg Glu Pro
                115                 120                 125

Gln Val Tyr Thr Leu Pro Pro Ser Arg Asp Glu Leu Thr Lys Asn Gln
                130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175
```

```
Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
210                 215                 220

Leu Ser Pro Gly
225

<210> SEQ ID NO 3
<211> LENGTH: 205
<212> TYPE: PRT
<213> ORGANISM: Homo sapiens

<400> SEQUENCE: 3

Gly Asp Thr Gly Arg Pro Phe Val Glu Met Tyr Ser Glu Ile Pro Glu
1               5                   10                  15

Ile Ile His Met Thr Glu Gly Arg Glu Leu Val Ile Pro Cys Arg Val
            20                  25                  30

Thr Ser Pro Asn Ile Thr Val Thr Leu Lys Lys Phe Pro Leu Asp Thr
        35                  40                  45

Leu Ile Pro Asp Gly Lys Arg Ile Ile Trp Asp Ser Arg Lys Gly Phe
    50                  55                  60

Ile Ile Ser Asn Ala Thr Tyr Lys Glu Ile Gly Leu Leu Thr Cys Glu
65                  70                  75                  80

Ala Thr Val Asn Gly His Leu Tyr Lys Thr Asn Tyr Leu Thr His Arg
                85                  90                  95

Gln Thr Asn Thr Ile Ile Asp Val Val Leu Ser Pro Ser His Gly Ile
            100                 105                 110

Glu Leu Ser Val Gly Glu Lys Leu Val Leu Asn Cys Thr Ala Arg Thr
        115                 120                 125

Glu Leu Asn Val Gly Ile Asp Phe Asn Trp Glu Tyr Pro Ser Ser Lys
    130                 135                 140

His Gln His Lys Lys Leu Val Asn Arg Asp Leu Lys Thr Gln Ser Gly
145                 150                 155                 160

Ser Glu Met Lys Lys Phe Leu Ser Thr Leu Thr Ile Asp Gly Val Thr
                165                 170                 175

Arg Ser Asp Gln Gly Leu Tyr Thr Cys Ala Ala Ser Ser Gly Leu Met
            180                 185                 190

Thr Lys Lys Asn Ser Thr Phe Val Arg Val His Glu Lys
        195                 200                 205

<210> SEQ ID NO 4
<211> LENGTH: 15
<212> TYPE: PRT
<213> ORGANISM: Homo sapiens

<400> SEQUENCE: 4

Gly Gly Gly Gly Ser Gly Gly Gly Gly Ser Gly Gly Gly Gly Ser
1               5                   10                  15

<210> SEQ ID NO 5
<211> LENGTH: 123
<212> TYPE: PRT
<213> ORGANISM: Homo sapiens

<400> SEQUENCE: 5

Glu Val Gln Leu Val Glu Ser Gly Gly Gly Leu Val Gln Pro Gly Gly
```

```
                1               5                  10                 15
            Ser Leu Arg Leu Ser Cys Ala Ala Ser Gly Tyr Asp Phe Thr His Tyr
                            20                  25                  30

Gly Met Asn Trp Val Arg Gln Ala Pro Gly Lys Gly Leu Glu Trp Val
                            35                  40                  45

Gly Trp Ile Asn Thr Tyr Thr Gly Glu Pro Thr Tyr Ala Ala Asp Phe
                        50                  55                  60

Lys Arg Arg Phe Thr Phe Ser Leu Asp Thr Ser Lys Ser Thr Ala Tyr
             65                 70                  75                  80

Leu Gln Met Asn Ser Leu Arg Ala Glu Asp Thr Ala Val Tyr Tyr Cys
                            85                  90                  95

Ala Lys Tyr Pro Tyr Tyr Tyr Gly Thr Ser His Trp Tyr Phe Asp Val
                            100                 105                 110

Trp Gly Gln Gly Thr Leu Val Thr Val Ser Ser
                            115                 120
```

<210> SEQ ID NO 6
<211> LENGTH: 107
<212> TYPE: PRT
<213> ORGANISM: Homo sapiens

<400> SEQUENCE: 6

```
            Asp Ile Gln Leu Thr Gln Ser Pro Ser Ser Leu Ser Ala Ser Val Gly
             1               5                  10                  15

Asp Arg Val Thr Ile Thr Cys Ser Ala Ser Gln Asp Ile Ser Asn Tyr
                            20                  25                  30

Leu Asn Trp Tyr Gln Gln Lys Pro Gly Lys Ala Pro Lys Val Leu Ile
                            35                  40                  45

Tyr Phe Thr Ser Ser Leu His Ser Gly Val Pro Ser Arg Phe Ser Gly
                        50                  55                  60

Ser Gly Ser Gly Thr Asp Phe Thr Leu Thr Ile Ser Ser Leu Gln Pro
             65                 70                  75                  80

Glu Asp Phe Ala Thr Tyr Tyr Cys Gln Gln Tyr Ser Thr Val Pro Trp
                            85                  90                  95

Thr Phe Gly Gln Gly Thr Lys Val Glu Ile Lys
                            100                 105
```

<210> SEQ ID NO 7
<211> LENGTH: 229
<212> TYPE: PRT
<213> ORGANISM: Homo sapiens

<400> SEQUENCE: 7

```
            Glu Val Gln Leu Val Glu Ser Gly Gly Gly Leu Val Gln Pro Gly Arg
             1               5                  10                  15

Ser Leu Arg Leu Ser Cys Ala Ala Ser Gly Phe Thr Phe Asp Asp Tyr
                            20                  25                  30

Ala Met His Trp Val Arg Gln Ala Pro Gly Lys Gly Leu Glu Trp Val
                            35                  40                  45

Ser Gly Ile Ser Trp Asn Ser Gly Ser Ile Gly Tyr Ala Asp Ser Val
                        50                  55                  60

Lys Gly Arg Phe Thr Ile Ser Arg Asp Asn Ala Lys Asn Ser Leu Tyr
             65                 70                  75                  80

Leu Gln Met Asn Ser Leu Arg Ala Glu Asp Thr Ala Leu Tyr Tyr Cys
                            85                  90                  95

Ala Lys Asp Ile Gly Gly Ile Val Gly Ala Ala Thr Leu Gly Asp Ala
```

```
            100                 105                 110
Phe Asp Ile Trp Gly Gln Gly Thr Met Val Thr Val Ser Ser Ala Ser
        115                 120                 125

Thr Lys Gly Pro Ser Val Phe Pro Leu Ala Pro Ser Ser Lys Ser Thr
    130                 135                 140

Ser Gly Gly Thr Ala Ala Leu Gly Cys Leu Val Lys Asp Tyr Phe Pro
145                 150                 155                 160

Glu Pro Val Thr Val Ser Trp Asn Ser Gly Ala Leu Thr Ser Gly Val
                165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
        195                 200                 205

Cys Asn Val Asn His Lys Pro Ser Asn Thr Lys Val Asp Lys Lys Val
210                 215                 220

Glu Pro Lys Ser Cys
225

<210> SEQ ID NO 8
<211> LENGTH: 212
<212> TYPE: PRT
<213> ORGANISM: Homo sapiens

<400> SEQUENCE: 8

Ser Tyr Glu Leu Thr Gln Pro Pro Ser Val Ser Val Ser Pro Gly Gln
1               5                   10                  15

Thr Ala Ser Ile Thr Cys Ser Gly Asp Glu Leu Gly Glu Lys Tyr Ala
            20                  25                  30

Ser Trp Tyr Gln Gln Lys Pro Gly Gln Ser Pro Val Leu Val Ile Tyr
        35                  40                  45

Gln Asp Ser Lys Arg Pro Ser Gly Ile Pro Glu Arg Phe Ser Gly Ser
    50                  55                  60

Asn Ser Gly Asn Thr Ala Thr Leu Thr Ile Ser Gly Thr Gln Ala Met
65                  70                  75                  80

Asp Glu Ala Asp Tyr Tyr Cys Gln Ala Trp Asp Ser Ser Thr Ala Val
                85                  90                  95

Phe Gly Gly Gly Thr Lys Leu Thr Val Leu Gly Gln Pro Lys Ala Ala
            100                 105                 110

Pro Ser Val Thr Leu Phe Pro Pro Ser Ser Glu Glu Leu Gln Ala Asn
        115                 120                 125

Lys Ala Thr Leu Val Cys Leu Ile Ser Asp Phe Tyr Pro Gly Ala Val
    130                 135                 140

Thr Val Ala Trp Lys Ala Asp Ser Ser Pro Val Lys Ala Gly Val Glu
145                 150                 155                 160

Thr Thr Thr Pro Ser Lys Gln Ser Asn Asn Lys Tyr Ala Ala Ser Ser
                165                 170                 175

Tyr Leu Ser Leu Thr Pro Glu Gln Trp Lys Ser His Arg Ser Tyr Ser
            180                 185                 190

Cys Gln Val Thr His Glu Gly Ser Thr Val Glu Lys Thr Val Ala Pro
        195                 200                 205

Ala Glu Cys Ser
    210

<210> SEQ ID NO 9
<211> LENGTH: 20
```

```
<212> TYPE: PRT
<213> ORGANISM: Homo sapiens

<400> SEQUENCE: 9
```

Met Glu Thr Asp Thr Leu Leu Leu Trp Val Leu Leu Leu Trp Val Pro
1               5                   10                  15

Gly Ser Thr Gly
            20

```
<210> SEQ ID NO 10
<211> LENGTH: 655
<212> TYPE: PRT
<213> ORGANISM: Homo sapiens

<400> SEQUENCE: 10
```

Ala Met Asp Leu Ile Leu Ile Asn Ser Leu Pro Leu Val Ser Asp Ala
1               5                   10                  15

Glu Thr Ser Leu Thr Cys Ile Ala Ser Gly Trp Arg Pro His Glu Pro
            20                  25                  30

Ile Thr Ile Gly Arg Asp Phe Glu Ala Leu Met Asn Gln His Gln Asp
        35                  40                  45

Pro Leu Glu Val Thr Gln Asp Val Thr Arg Glu Trp Ala Lys Lys Val
50                  55                  60

Val Trp Lys Arg Glu Lys Ala Ser Lys Ile Asn Gly Ala Tyr Phe Cys
65                  70                  75                  80

Glu Gly Arg Val Arg Gly Glu Ala Ile Arg Ile Arg Thr Met Lys Met
                85                  90                  95

Arg Gln Gln Ala Ser Phe Leu Pro Ala Thr Leu Thr Met Thr Val Asp
            100                 105                 110

Lys Gly Asp Asn Val Asn Ile Ser Phe Lys Lys Val Leu Ile Lys Glu
        115                 120                 125

Glu Asp Ala Val Ile Tyr Lys Asn Gly Ser Phe Ile His Ser Val Pro
130                 135                 140

Arg His Glu Val Pro Asp Ile Leu Glu Val His Leu Pro His Ala Gln
145                 150                 155                 160

Pro Gln Asp Ala Gly Val Tyr Ser Ala Arg Tyr Ile Gly Gly Asn Leu
                165                 170                 175

Phe Thr Ser Ala Phe Thr Arg Leu Ile Val Arg Arg Cys Glu Ala Gln
            180                 185                 190

Lys Trp Gly Pro Glu Cys Asn His Leu Cys Thr Ala Cys Met Asn Asn
        195                 200                 205

Gly Val Cys His Glu Asp Thr Gly Glu Cys Ile Cys Pro Pro Gly Phe
210                 215                 220

Met Gly Arg Thr Cys Glu Lys Ala Cys Glu Leu His Thr Phe Gly Arg
225                 230                 235                 240

Thr Cys Lys Glu Arg Cys Ser Gly Gln Glu Gly Cys Lys Ser Tyr Val
                245                 250                 255

Phe Cys Leu Pro Asp Pro Tyr Gly Cys Ser Cys Ala Thr Gly Trp Lys
            260                 265                 270

Gly Leu Gln Cys Asn Glu Ala Cys His Pro Gly Phe Tyr Gly Pro Asp
        275                 280                 285

Cys Lys Leu Arg Cys Ser Cys Asn Asn Gly Glu Met Cys Asp Arg Phe
290                 295                 300

Gln Gly Cys Leu Cys Ser Pro Gly Trp Gln Gly Leu Gln Cys Glu Arg
305                 310                 315                 320

```
Glu Gly Ile Gln Arg Met Thr Pro Lys Ile Val Asp Leu Pro Asp His
            325                 330                 335

Ile Glu Val Asn Ser Gly Lys Phe Asn Pro Ile Cys Lys Ala Ser Gly
            340                 345                 350

Trp Pro Leu Pro Thr Asn Glu Glu Met Thr Leu Val Lys Pro Asp Gly
            355                 360                 365

Thr Val Leu His Pro Lys Asp Phe Asn His Thr Asp His Phe Ser Val
            370                 375                 380

Ala Ile Phe Thr Ile His Arg Ile Leu Pro Pro Asp Ser Gly Val Trp
385                 390                 395                 400

Val Cys Ser Val Asn Thr Val Ala Gly Met Val Glu Lys Pro Phe Asn
                405                 410                 415

Ile Ser Val Lys Val Leu Pro Lys Pro Leu Ala Ser Asp Lys Thr His
                420                 425                 430

Thr Cys Pro Pro Cys Pro Ala Pro Glu Leu Leu Gly Gly Pro Ser Val
            435                 440                 445

Phe Leu Phe Pro Pro Lys Pro Lys Asp Thr Leu Met Ile Ser Arg Thr
            450                 455                 460

Pro Glu Val Thr Cys Val Val Val Asp Val Ser His Glu Asp Pro Glu
465                 470                 475                 480

Val Lys Phe Asn Trp Tyr Val Asp Gly Val Glu Val His Asn Ala Lys
                485                 490                 495

Thr Lys Pro Arg Glu Glu Gln Tyr Asn Ser Thr Tyr Arg Val Val Ser
                500                 505                 510

Val Leu Thr Val Leu His Gln Asp Trp Leu Asn Gly Lys Glu Tyr Lys
            515                 520                 525

Cys Lys Val Ser Asn Lys Ala Leu Pro Ala Pro Ile Glu Lys Thr Ile
            530                 535                 540

Ser Lys Ala Lys Gly Gln Pro Arg Glu Pro Gln Val Tyr Thr Leu Pro
545                 550                 555                 560

Pro Ser Arg Asp Glu Leu Thr Lys Asn Gln Val Ser Leu Thr Cys Leu
                565                 570                 575

Val Lys Gly Phe Tyr Pro Ser Asp Ile Ala Val Glu Trp Glu Ser Asn
                580                 585                 590

Gly Gln Pro Glu Asn Asn Tyr Lys Thr Thr Pro Pro Val Leu Asp Ser
            595                 600                 605

Asp Gly Ser Phe Phe Leu Tyr Ser Lys Leu Thr Val Asp Lys Ser Arg
            610                 615                 620

Trp Gln Gln Gly Asn Val Phe Ser Cys Ser Val Met His Glu Ala Leu
625                 630                 635                 640

His Asn His Tyr Thr Gln Lys Ser Leu Ser Leu Ser Pro Gly Lys
                645                 650                 655

<210> SEQ ID NO 11
<211> LENGTH: 448
<212> TYPE: PRT
<213> ORGANISM: Homo sapiens

<400> SEQUENCE: 11

Ala Ser Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
            35                  40                  45
```

Ser His Glu Asp Pro Glu Val Lys Phe Asn Trp Tyr Val Asp Gly Val
 50                  55                  60

Glu Val His Asn Ala Lys Thr Lys Pro Arg Glu Gln Tyr Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
            115                 120                 125

Gln Val Tyr Thr Leu Pro Pro Ser Arg Asp Glu Leu Thr Lys Asn Gln
130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
            195                 200                 205

Val Met His Glu Ala Leu His Asn His Tyr Thr Gln Lys Ser Leu Ser
210                 215                 220

Leu Ser Pro Gly Gly Gly Gly Ser Gly Gly Gly Gly Ser Gly Gly
225                 230                 235                 240

Gly Gly Ser Gly Asp Thr Gly Arg Pro Phe Val Glu Met Tyr Ser Glu
                245                 250                 255

Ile Pro Glu Ile Ile His Met Thr Glu Gly Arg Glu Leu Val Ile Pro
            260                 265                 270

Cys Arg Val Thr Ser Pro Asn Ile Thr Val Thr Leu Lys Lys Phe Pro
            275                 280                 285

Leu Asp Thr Leu Ile Pro Asp Gly Lys Arg Ile Ile Trp Asp Ser Arg
290                 295                 300

Lys Gly Phe Ile Ile Ser Asn Ala Thr Tyr Lys Glu Ile Gly Leu Leu
305                 310                 315                 320

Thr Cys Glu Ala Thr Val Asn Gly His Leu Tyr Lys Thr Asn Tyr Leu
                325                 330                 335

Thr His Arg Gln Thr Asn Thr Ile Ile Asp Val Val Leu Ser Pro Ser
            340                 345                 350

His Gly Ile Glu Leu Ser Val Gly Glu Lys Leu Val Leu Asn Cys Thr
            355                 360                 365

Ala Arg Thr Glu Leu Asn Val Gly Ile Asp Phe Asn Trp Glu Tyr Pro
370                 375                 380

Ser Ser Lys His Gln His Lys Lys Leu Val Asn Arg Asp Leu Lys Thr
385                 390                 395                 400

Gln Ser Gly Ser Glu Met Lys Lys Phe Leu Ser Thr Leu Thr Ile Asp
                405                 410                 415

Gly Val Thr Arg Ser Asp Gln Gly Leu Tyr Thr Cys Ala Ala Ser Ser
            420                 425                 430

Gly Leu Met Thr Lys Lys Asn Ser Thr Phe Val Arg Val His Glu Lys
            435                 440                 445

<210> SEQ ID NO 12
<211> LENGTH: 874

<212> TYPE: PRT
<213> ORGANISM: Homo sapiens

<400> SEQUENCE: 12

Ala Met Asp Leu Ile Leu Ile Asn Ser Leu Pro Leu Val Ser Asp Ala
1               5                   10                  15

Glu Thr Ser Leu Thr Cys Ile Ala Ser Gly Trp Arg Pro His Glu Pro
            20                  25                  30

Ile Thr Ile Gly Arg Asp Phe Glu Ala Leu Met Asn Gln His Gln Asp
        35                  40                  45

Pro Leu Glu Val Thr Gln Asp Val Thr Arg Glu Trp Ala Lys Lys Val
    50                  55                  60

Val Trp Lys Arg Glu Lys Ala Ser Lys Ile Asn Gly Ala Tyr Phe Cys
65                  70                  75                  80

Glu Gly Arg Val Arg Gly Glu Ala Ile Arg Ile Arg Thr Met Lys Met
                85                  90                  95

Arg Gln Gln Ala Ser Phe Leu Pro Ala Thr Leu Thr Met Thr Val Asp
            100                 105                 110

Lys Gly Asp Asn Val Asn Ile Ser Phe Lys Lys Val Leu Ile Lys Glu
        115                 120                 125

Glu Asp Ala Val Ile Tyr Lys Asn Gly Ser Phe Ile His Ser Val Pro
    130                 135                 140

Arg His Glu Val Pro Asp Ile Leu Glu Val His Leu Pro His Ala Gln
145                 150                 155                 160

Pro Gln Asp Ala Gly Val Tyr Ser Ala Arg Tyr Ile Gly Gly Asn Leu
                165                 170                 175

Phe Thr Ser Ala Phe Thr Arg Leu Ile Val Arg Arg Cys Glu Ala Gln
            180                 185                 190

Lys Trp Gly Pro Glu Cys Asn His Leu Cys Thr Ala Cys Met Asn Asn
        195                 200                 205

Gly Val Cys His Glu Asp Thr Gly Glu Cys Ile Cys Pro Pro Gly Phe
    210                 215                 220

Met Gly Arg Thr Cys Glu Lys Ala Cys Glu Leu His Thr Phe Gly Arg
225                 230                 235                 240

Thr Cys Lys Glu Arg Cys Ser Gly Gln Glu Gly Cys Lys Ser Tyr Val
                245                 250                 255

Phe Cys Leu Pro Asp Pro Tyr Gly Cys Ser Cys Ala Thr Gly Trp Lys
            260                 265                 270

Gly Leu Gln Cys Asn Glu Ala Cys His Pro Gly Phe Tyr Gly Pro Asp
        275                 280                 285

Cys Lys Leu Arg Cys Ser Cys Asn Asn Gly Glu Met Cys Asp Arg Phe
    290                 295                 300

Gln Gly Cys Leu Cys Ser Pro Gly Trp Gln Gly Leu Gln Cys Glu Arg
305                 310                 315                 320

Glu Gly Ile Gln Arg Met Thr Pro Lys Ile Val Asp Leu Pro Asp His
                325                 330                 335

Ile Glu Val Asn Ser Gly Lys Phe Asn Pro Ile Cys Lys Ala Ser Gly
            340                 345                 350

Trp Pro Leu Pro Thr Asn Glu Glu Met Thr Leu Val Lys Pro Asp Gly
        355                 360                 365

Thr Val Leu His Pro Lys Asp Phe Asn His Thr Asp His Phe Ser Val
    370                 375                 380

Ala Ile Phe Thr Ile His Arg Ile Leu Pro Pro Asp Ser Gly Val Trp
385                 390                 395                 400

-continued

```
Val Cys Ser Val Asn Thr Val Ala Gly Met Val Glu Lys Pro Phe Asn
            405                 410                 415
Ile Ser Val Lys Val Leu Pro Lys Pro Leu Ala Ser Asp Lys Thr His
            420                 425                 430
Thr Cys Pro Pro Cys Pro Ala Pro Glu Leu Leu Gly Gly Pro Ser Val
            435                 440                 445
Phe Leu Phe Pro Pro Lys Pro Lys Asp Thr Leu Met Ile Ser Arg Thr
450                 455                 460
Pro Glu Val Thr Cys Val Val Asp Val Ser His Glu Asp Pro Glu
465                 470                 475                 480
Val Lys Phe Asn Trp Tyr Val Asp Gly Val Glu Val His Asn Ala Lys
            485                 490                 495
Thr Lys Pro Arg Glu Glu Gln Tyr Asn Ser Thr Tyr Arg Val Val Ser
            500                 505                 510
Val Leu Thr Val Leu His Gln Asp Trp Leu Asn Gly Lys Glu Tyr Lys
            515                 520                 525
Cys Lys Val Ser Asn Lys Ala Leu Pro Ala Pro Ile Glu Lys Thr Ile
            530                 535                 540
Ser Lys Ala Lys Gly Gln Pro Arg Glu Pro Gln Val Tyr Thr Leu Pro
545                 550                 555                 560
Pro Ser Arg Asp Glu Leu Thr Lys Asn Gln Val Ser Leu Thr Cys Leu
                        565                 570                 575
Val Lys Gly Phe Tyr Pro Ser Asp Ile Ala Val Glu Trp Glu Ser Asn
            580                 585                 590
Gly Gln Pro Glu Asn Asn Tyr Lys Thr Thr Pro Pro Val Leu Asp Ser
            595                 600                 605
Asp Gly Ser Phe Phe Leu Tyr Ser Lys Leu Thr Val Asp Lys Ser Arg
            610                 615                 620
Trp Gln Gln Gly Asn Val Phe Ser Cys Ser Val Met His Glu Ala Leu
625                 630                 635                 640
His Asn His Tyr Thr Gln Lys Ser Leu Ser Leu Ser Pro Gly Gly Gly
                        645                 650                 655
Gly Gly Ser Gly Gly Gly Gly Ser Gly Gly Gly Gly Ser Gly Asp Thr
            660                 665                 670
Gly Arg Pro Phe Val Glu Met Tyr Ser Glu Ile Pro Glu Ile Ile His
            675                 680                 685
Met Thr Glu Gly Arg Glu Leu Val Ile Pro Cys Arg Val Thr Ser Pro
690                 695                 700
Asn Ile Thr Val Thr Leu Lys Lys Phe Pro Leu Asp Thr Leu Ile Pro
705                 710                 715                 720
Asp Gly Lys Arg Ile Ile Trp Asp Ser Arg Lys Gly Phe Ile Ile Ser
            725                 730                 735
Asn Ala Thr Tyr Lys Glu Ile Gly Leu Leu Thr Cys Glu Ala Thr Val
            740                 745                 750
Asn Gly His Leu Tyr Lys Thr Asn Tyr Leu Thr His Arg Gln Thr Asn
            755                 760                 765
Thr Ile Ile Asp Val Val Leu Ser Pro Ser His Gly Ile Glu Leu Ser
            770                 775                 780
Val Gly Glu Lys Leu Val Leu Asn Cys Thr Ala Arg Thr Glu Leu Asn
785                 790                 795                 800
Val Gly Ile Asp Phe Asn Trp Glu Tyr Pro Ser Ser Lys His Gln His
                        805                 810                 815
```

```
Lys Lys Leu Val Asn Arg Asp Leu Lys Thr Gln Ser Gly Ser Glu Met
            820                 825                 830

Lys Lys Phe Leu Ser Thr Leu Thr Ile Asp Gly Val Thr Arg Ser Asp
            835                 840                 845

Gln Gly Leu Tyr Thr Cys Ala Ala Ser Ser Gly Leu Met Thr Lys Lys
            850                 855                 860

Asn Ser Thr Phe Val Arg Val His Glu Lys
865                 870

<210> SEQ ID NO 13
<211> LENGTH: 496
<212> TYPE: PRT
<213> ORGANISM: Homo sapiens

<400> SEQUENCE: 13

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Ala Pro Gly Lys Gly Leu Glu Trp Val
            35                  40                  45

Ser Gly Ile Ser Trp Asn Ser Gly Ser Ile Gly Tyr Ala Asp Ser Val
            50                  55                  60

Lys Gly Arg Phe Thr Ile Ser Arg Asp Asn Ala Lys Asn Ser Leu Tyr
65              70                  75                  80

Leu Gln Met Asn Ser Leu Arg Ala Glu Asp Thr Ala Leu Tyr Tyr Cys
            85                  90                  95

Ala Lys Asp Ile Gly Gly Ile Val Gly Ala Ala Thr Leu Gly Asp Ala
            100                 105                 110

Phe Asp Ile Trp Gly Gln Gly Thr Met Val Thr Val Ser Ser Ala Ser
            115                 120                 125

Thr Lys Gly Pro Ser Val Phe Pro Leu Ala Pro Ser Ser Lys Ser Thr
            130                 135                 140

Ser Gly Gly Thr Ala Ala Leu Gly Cys Leu Val Lys Asp Tyr Phe Pro
145             150                 155                 160

Glu Pro Val Thr Val Ser Trp Asn Ser Gly Ala Leu Thr Ser Gly Val
            165                 170                 175

His Thr Phe Pro Ala Val Leu Gln Ser Ser Gly Leu Tyr Ser Leu Ser
            180                 185                 190

Ser Val Val Thr Val Pro Ser Ser Ser Leu Gly Thr Gln Thr Tyr Ile
            195                 200                 205

Cys Asn Val Asn His Lys Pro Ser Asn Thr Lys Val Asp Lys Lys Val
            210                 215                 220

Glu Pro Lys Ser Cys Gly Gly Gly Gly Ser Gly Gly Gly Gly Ser
225             230                 235                 240

Gly Gly Gly Gly Ser Glu Val Gln Leu Val Glu Ser Gly Gly Gly Leu
            245                 250                 255

Val Gln Pro Gly Gly Ser Leu Arg Leu Ser Cys Ala Ala Ser Gly Tyr
            260                 265                 270

Asp Phe Thr His Tyr Gly Met Asn Trp Val Arg Gln Ala Pro Gly Lys
            275                 280                 285

Gly Leu Glu Trp Val Gly Trp Ile Asn Thr Tyr Thr Gly Glu Pro Thr
            290                 295                 300

Tyr Ala Ala Asp Phe Lys Arg Arg Phe Thr Phe Ser Leu Asp Thr Ser
305             310                 315                 320
```

-continued

```
Lys Ser Thr Ala Tyr Leu Gln Met Asn Ser Leu Arg Ala Glu Asp Thr
            325                 330                 335

Ala Val Tyr Tyr Cys Ala Lys Tyr Pro Tyr Tyr Tyr Gly Thr Ser His
            340                 345                 350

Trp Tyr Phe Asp Val Trp Gly Gln Gly Thr Leu Val Thr Val Ser Ser
            355                 360                 365

Gly Gly Gly Gly Ser Gly Gly Gly Gly Ser Gly Gly Gly Gly Ser Asp
            370                 375                 380

Ile Gln Leu Thr Gln Ser Pro Ser Ser Leu Ser Ala Ser Val Gly Asp
385                 390                 395                 400

Arg Val Thr Ile Thr Cys Ser Ala Ser Gln Asp Ile Ser Asn Tyr Leu
            405                 410                 415

Asn Trp Tyr Gln Gln Lys Pro Gly Lys Ala Pro Lys Val Leu Ile Tyr
            420                 425                 430

Phe Thr Ser Ser Leu His Ser Gly Val Pro Ser Arg Phe Ser Gly Ser
            435                 440                 445

Gly Ser Gly Thr Asp Phe Thr Leu Thr Ile Ser Ser Leu Gln Pro Glu
            450                 455                 460

Asp Phe Ala Thr Tyr Tyr Cys Gln Gln Tyr Ser Thr Val Pro Trp Thr
465                 470                 475                 480

Phe Gly Gln Gly Thr Lys Val Glu Ile Lys His His His His His His
            485                 490                 495
```